US006861438B2

(12) United States Patent
Larsen et al.

(10) Patent No.: US 6,861,438 B2
(45) Date of Patent: Mar. 1, 2005

(54) ANTIVIRAL AGENTS

(75) Inventors: Scott D. Larsen, Kalamazoo, MI (US); Paul May, Richland, MI (US); Karen Romines, Durham, NC (US); Mark E. Schnute, Kalamazoo, MI (US); Steven P. Tanis, Kalamazoo, MI (US)

(73) Assignee: Pfizer, Bridgewater, NJ (US)

( * ) Notice: Subject to any disclaimer, the term of this patent is extended or adjusted under 35 U.S.C. 154(b) by 0 days.

(21) Appl. No.: 10/345,095

(22) Filed: Jan. 14, 2003

(65) Prior Publication Data

US 2004/0138449 A1 Jul. 15, 2004

Related U.S. Application Data

(60) Provisional application No. 60/348,865, filed on Jan. 14, 2002.

(51) Int. Cl.[7] ..................... C07D 495/04; A61K 31/435
(52) U.S. Cl. ....................................... 514/301; 546/114
(58) Field of Search ........................... 546/114; 514/301

(56) References Cited

U.S. PATENT DOCUMENTS

| | | | | |
|---|---|---|---|---|
| 4,125,611 | A | 11/1978 | Yamade et al. | 424/246 |
| 4,145,418 | A | 3/1979 | Kuwada et al. | 424/246 |
| 4,767,766 | A | 8/1988 | Baker et al. | 514/301 |
| 4,877,793 | A | * 10/1989 | Davies | 514/301 |
| 4,959,363 | A | 9/1990 | Wentland | 514/235.2 |
| 5,155,115 | A | 10/1992 | Suzuki et al. | 514/301 |
| 5,219,864 | A | 6/1993 | Suzuki et al. | 514/301 |
| 5,352,685 | A | 10/1994 | Maruyama et al. | 514/301 |
| 5,593,943 | A | 1/1997 | Nuebling et al. | 504/221 |
| 5,817,819 | A | 10/1998 | Furuya et al. | 546/114 |
| 6,239,142 | B1 | 5/2001 | Schnute et al. | 514/301 |
| 6,620,810 | B2 | 9/2003 | Thorarensen | 514/233.8 |

FOREIGN PATENT DOCUMENTS

| | | | | |
|---|---|---|---|---|
| DE | 4227747 | 2/1994 | ......... | C07D/487/04 |
| EP | 0046990 | 3/1982 | ......... | C07D/495/04 |
| EP | 0269295 | 6/1988 | ......... | C07D/495/04 |
| EP | 0443568 | 2/1991 | ......... | C07D/495/04 |
| EP | 505058 | 9/1992 | ......... | C07D/495/04 |
| EP | 0560348 | 9/1993 | ......... | C07D/519/00 |
| GB | 2289276 | 11/1995 | ....... | C07D/491/408 |
| JP | 46-032198 | 9/1970 | | |
| JP | 57116077 | 7/1982 | ......... | C07D/495/04 |
| JP | 57142985 | 9/1982 | ......... | C07D/495/04 |
| JP | 07076586 A | 3/1995 | ....... | C07D/491/048 |
| JP | 07076586 | 3/1995 | ....... | C07D/491/408 |
| JP | 08301849 A | 11/1996 | ......... | C07D/217/26 |
| JP | 08301849 | 11/1996 | ......... | C07D/217/26 |
| WO | WO-92/03427 | 3/1992 | ......... | C07D/307/82 |
| WO | WO-95/28405 | 10/1995 | ......... | C07D/495/04 |
| WO | WO-96/18616 | 6/1996 | ......... | C07D/213/75 |
| WO | WO-96/18617 | 6/1996 | ......... | C07D/213/75 |
| WO | WO-97/40846 | 11/1997 | .......... | A61K/38/09 |
| WO | WO-98/11073 | 3/1998 | ......... | C07D/215/48 |
| WO | WO-99/32450 | 7/1999 | ......... | C07D/215/56 |
| WO | WO-99/62908 | 12/1999 | ......... | C07D/495/04 |
| WO | WO-00/07595 | 2/2000 | .......... | A61K/31/47 |
| WO | WO-00/40561 | 7/2000 | ......... | C07D/215/16 |
| WO | WO-00/40563 | 7/2000 | ......... | C07D/215/56 |
| WO | WO-00/53610 | 9/2000 | ......... | C07D/513/04 |
| WO | WO-00/76990 | 12/2000 | ......... | C07D/307/78 |
| WO | WO-01/37824 | 5/2001 | ......... | A61K/31/315 |
| WO | WO-01/58898 | 8/2001 | ......... | C07D/453/02 |
| WO | WO-03/020729 | 3/2003 | ......... | C07D/495/04 |

OTHER PUBLICATIONS

*Database Crossfire Beilstein*, vol. 26, No. 1, Beilstein Institut zur Foerderung der chemischen Wissenschaften,Frankfurt am Main, DE (1991), 3 pages.
*Database Crossfire Beilstein*, vol. 21, Beilstein Institut zur Foerderung der chemischen Wissenschaften,Frankfurt am Main, DE (1984) 3 pages.
*The Merck Manual of Diagnosis and Therapy, Eleventh Edition*, Lyght, C.E., et al., (eds.), Merck & Co.,(1966), pp. 212–213.
Blaskiewicz, P. , et al., "Thienopyridinonecarboxylic Acid Derivatives", *Chemical Abstracts*, Abstract of German Patent No. 2,447,477, Abstract No. 85:46627, (1976), 2 pgs.
El–Abadelah, Mustafa M., et al., "Synthesis and Chiroptical Properties of Some N–(2–Chloro–7–cyclopropyl–4, 7–dihydro–4–oxo–thieno[2,3–b]pyridine–5–carbonyl) L–a–Amino Ester", *Z. Naturforsch*, (1977), pp. 419–426.
Elliott, Richard L., et al., "The Preparation of 2–(Heterocyclyl)thieno[3,2–b]pyridine Derivatives", *Tetrahedron*, vol. 43, No. 14, (1987), pp. 3295–3302.
Goerlitzer, K. , et al., "Gyrase inhibitors; Part 3.: Synthesis and reactions of ethyl 1,4–dihydro–4–oxo[1]benzothieno[3, 2–b]pyridine–3–carboxylate",*Pharmazie*, vol. 55, No. 8, (2000), pp. 595–600.
Nishikawa, Yoshinori , et al., "Synthesis and Antiallergic Activity of N–[4–(4–Diphenylmethyl–1–piperazinyl) butyl]–1,4–dihydro–4–oxopyridine–3–carboxamides", *Chem. Pharm. Bull.*, vol. 37, No. 5, (1989), pp. 1256–1259.

(List continued on next page.)

*Primary Examiner*—Bruce Kifle
(74) *Attorney, Agent, or Firm*—Schwegman, Lundberg, Woessner & Kluth, P.A.

(57) ABSTRACT

The invention provides a compound of formula I:

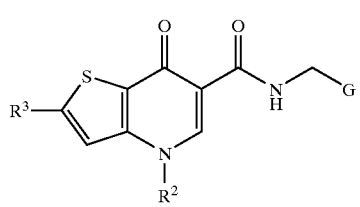

wherein G, $R^2$, and $R^3$ have any of the values defined in the specification, or a pharmaceutically acceptable salt thereof, as well as processes and intermediates useful for preparing such compounds or salts, and methods of treating a herpesvirus infection using such compounds or salts.

50 Claims, No Drawings

OTHER PUBLICATIONS

Patani, G. A., et al., "Bioisosterism: A Rational Approach in Drug Design", *Chemical Reviews,* 96(8), (1996), pp. 3147–3176.

Thornber, C. W., "Isosterism and Molecular Modification in Drug Design", *Chemical Socitey Review*, vol. 8, No. 4, (1979), pp. 563–580.

Vaillancourt, V A., et al., "Naphthalene carboxamides as inhibitors of human cytomegalovirus DNA polymerase", *Bioorganic& Medicinal Chemistry Letters*, vol. 10, No. 18 (2000), pp. 2079–2081.

* cited by examiner

ANTIVIRAL AGENTS

RELATED APPLICATIONS

This application claims priority to U.S. Provisional Patent Application Ser. No. 60/348,865, filed Jan. 14, 2002.

FIELD OF THE INVENTION

The present invention provides 7-oxo-4,7-dihydro-thieno[3,2-b]pyridine-6-carboxylic acid benzylamide derivatives that are useful as antivirals, for example, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, post-transplant lymphoproliferative disease (PTLD), and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Infection by or reactivation of herpesviruses is associated with several cardiovascular diseases or conditions in the host such as atherosclerosis and restenosis resulting in inflammation of coronary vessel walls. It is thought that in many patients suffering from restenosis following coronary atherectomy viral infection particularly by CMV plays an important role in the proliferation of the disease. Atherosclerosis is believed to be associated with the overall infectious disease burden in the host and particularly by the herpesviruses such as HSV, CMV, and EBV.

Infection in the animal population (livestock and companion) by strains of herpesviruses is endemic including cattle (Bovine herspesvirus 1–5, BHV), sheep (Ovine herpesvirus 1 and 2), dog (Canine herpesvirus 1), horse (Equine herpesvirus 1–8, EHV), cat (Feline herpesvirus 1, FHV), swine (pseudorabies virus, PRV), and many species of fowl. In the case of bovine herpesvirus infection, animals may suffer from ocular, respiratory, or digestive disorders. Pseudorabies is an extremely contagious viral pathogen infecting several species such as cattle, horses, dogs, cats, sheep, and goats leading to rapid death. The virus is benign in adult swine, however, it remains contagious and leads to high mortality in pigs under three weeks. Infection of horses by equine herpesvirus may lead to neurological syndromes, respiratory disease, and neonatal disease. Herpesvirus infection in cats leads to the disease known as feline viral rhinotracheitis (FVR) which is characterized by rhinitis, tracheitis, laryngitis, and conjunctivitis.

INFORMATION DISCLOSURE

JP 08301849 discloses heterocyclic carboxamide compounds which are reported to be useful as tachykinin receptor antagonists.

U.S. Pat. No. 6,239,142 discloses compounds having a thieno[2,3-b]pyridine core which are reported to be useful for the treatment of herpesvirus infections.

U.S. Pat. No. 5,352,685 discloses thieno[3,2-b]pyridine derivatives reported to be useful for the treatment of gastrointestinal disorders. The compounds are also reported to be useful for the treatment of anxiety and neuroses, and arrhythmia.

EP 269295 discloses thieno[3,2-b]pyridine compounds which are reported to be useful as cardiovascular agents.

EP 46990 discloses thieno[3,2-b]pyridine compounds which are reported to be useful as broad-spectrum antibacterials.

JP 57116077 discloses thieno[3,2-b]pyridine compounds which are reported to be useful as antibiotics.

JP 57142985 discloses thieno[3,2-b]pyridine compounds which are reported to be useful as antimicrobial agents.

In *Drugs Future*, 1999, 24, 966, there is disclosed a thieno[3,2-b]pyridine compound MKC-733 which is reported to be useful as a 5-$HT_3$ receptor agonist for the treatment of constipation and GERD.

In *Chem. Pharm. Bull.* 1989, 37, 1256, there is disclosed a thieno[3,2-b]pyridine compound 7 prepared and evaluated for anti-allergic activity. Compound 7 was reported to be inactive.

JP 08143573 A2 discloses thieno[3,2-b]pyridine compounds which are reported to be useful for treatment of intestinal dysfunction.

U.S. Pat. No. 5,155,115 discloses compounds including certain thieno[3,2-b]pyridine compounds which are reported to be useful as S3 antagonists for use as anti-emetics and anti-migraine agents.

U.S. Pat. No. 5,219,864 discloses compounds including certain thienopyridine compounds which are reported to be useful as immunoregulators and antiosteoporosis drugs.

In *Pharmazie* 2000, 55, 595, there is disclosed the preparation of certain thienopyridine compounds which are reported to be useful as gyrase inhibitors for the inhibition of growth of bacteria.

In *Tetrahedron* 1987, 43, 3295, there is disclosed the preparation of certain thienopyridine compounds as potential antibacterials.

WO 00/07595 discloses certain thienopyridine compounds which are reported to be useful to treat sexual dysfunction.

WO 97/40846 discloses a pharmaceutical comprising an LH releasing hormone agonist and an LH releasing hormone antagonist. The disclosed LH releasing hormone antagonists include an array of bicyclic compounds that include thienopyridines. The LH releasing hormone antagonists are not reported to possess any antiviral activity.

EP 505058 discloses thienopyridone compounds that are reported to possess immunoregulating and bone absorption inhibiting activity.

Despite the above teachings, there still exists a need for compounds with desirable antiviral activity.

SUMMARY OF THE INVENTION

1. The present invention provides a compound of formula I:

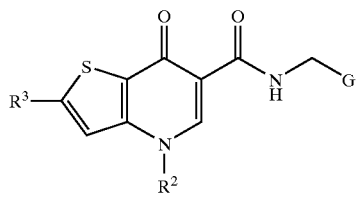

wherein:

G is phenyl substituted with from one to five $R^1$ substituents;

each $R^1$ is independently
(a) Cl,
(b) Br,
(c) F,
(d) cyano,
(d) $C_{1-7}$alkyl, or
(e) $NO_2$;

$R^2$ is
(a) H,
(b) $R^5$,
(c) $NR^7R^8$,
(d) $SO_2R^9$, or
(e) $OR^6$;

$R^3$ is
(a) H,
(b) halo,
(c) aryl,
(d) $S(O)_mR^6$,
(e) $(C=O)R^6$,
(f) $(C=O)OH$,
(g) $(C=O)OR^9$,
(h) cyano,
(i) het, wherein the het is bound via a carbon atom,
(j) $OR^{14}$,
(k) $NR^7R^8$,
(l) $SR^{14}$,
(m) $NHSO_2R^{12}$,
(n) $C_{1-7}$alkyl which is optionally partially unsaturated and optionally substituted by one or more $R^{11}$ substituents, or
(o) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^5$ is
(a) $(CH_2CH_2O)_tR^{10}$,
(b) het, wherein the het is bound via a carbon atom,
(c) aryl,
(d) $C_{1-7}$alkyl which is optionally partially unsaturated and optionally substituted by one or more $R^{11}$ substituents, or
(e) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^6$ is
(a) $C_{1-7}$alkyl optionally substituted by aryl, het, $OR^{13}$, $SR^{13}$, $NR^{13}R^{13}$, halo, or $C_{3-8}$cycloalkyl, which $C_{3-8}$cycloalkyl is optionally substituted with $OR^{13}$,
(b) $C_{3-8}$cycloalkyl which is optionally partially unsaturated and optionally substituted by one or more halo, $OR^{13}$, $SR^{13}$, or $NR^{13}R^{13}$ substituents,
(c) $NR^7R^8$,
(d) aryl, or
(e) het, wherein the het is bound via a carbon atom;

$R^7$ and $R^8$ are independently
(a) H,
(b) aryl,
(c) $C_{1-7}$alkyl which is optionally partially unsaturated and optionally substituted by one or more $NR^{13}R^{13}$, $OR^{14}$, $SR^{14}$, $S(O)_mR^9$, $P(=O)(OR^{14})(R^{14})$, $CONR^{14}R^{14}$, $CO_2R^{13}$, $(C=O)R^9$, het, aryl, cyano, or halo substituents,
(d) $C_{3-8}$cycloalkyl which is optionally partially unsaturated and optionally substituted by one or more halo, $OR^{13}$, $SR^{13}$, oxo, or $NR^{13}R^{13}$ substituents,
(e) $(C=O)R^9$, or
(f) $R^7$ and $R^8$ together with the nitrogen to which they are attached form a het;

$R^9$ is
(a) aryl,
(b) het
(c) $C_{3-8}$cycloalkyl, or
(d) $C_{1-7}$alkyl which is optionally partially unsaturated and optionally substituted by one or more $NR^{13}R^{13}$, $OR^{14}$, $SR^{14}$, halo, $CONR^{13}R^{13}$, $CO_2R^{13}$, het, or aryl substituents;

$R^{10}$ is
(a) H, or
(b) $C_{1-7}$alkyl optionally substituted by OH;

$R^{11}$ is
(a) $OR^{14}$,
(b) $SR^{14}$,
(c) $NR^7R^8$,
(d) halo,
(e) $CONH_2$,
(f) $CONHR^9$,
(g) $CONR^9R^9$,
(h) $CO_2H$,
(i) $CO_2R^9$,
(j) het,
(k) aryl,
(l) cyano,
(m) oxo,
(n) $SO_mR^6$, or
(o) $P(=O)(OR^{14})(R^{14})$;

$R^{12}$ is
(a) H,
(b) het,
(c) aryl,
(d) $C_{3-8}$cycloalkyl optionally substituted with $R^{11}$, or
(e) $C_{1-7}$alkyl optionally substituted with $R^{11}$;

$R^{13}$ is
(a) H, or
(b) $C_{1-7}$alkyl;

$R^{14}$ is
(a) H,
(b) aryl,
(c) het,
(d) $C_{1-7}$alkyl which is optionally partially unsaturated and optionally substituted by aryl, het, $OR^{13}$, $SR^{13}$, $NR^{13}R^{13}$, halo, or $C_{3-8}$cycloalkyl which $C_{3-8}$cycloalkyl is optionally substituted by one or more $OR^{13}$, or
(e) $C_{3-8}$cycloalkyl which is optionally partially unsaturated and optionally substituted by one or more halo, $OR^{13}$, $SR^{13}$, or $NR^{13}R^{13}$ substituents;

$R^{15}$ is
- (a) H,
- (b) halo,
- (c) $OR^{13}$,
- (d) $SR^{13}$,
- (e) $NR^{13}R^{13}$,
- (f) $O(CH_2CH_2O)_nR^{10}$,
  - a. phenyl,
  - b. cyano,
  - c. nitro,
  - d. $CONR^{13}R^{13}$,
  - e. $CO_2R^{13}$,
  - f. $S(O)_mNR^{13}R^{13}$,
  - g. $CONHR^{13}$,
  - h. $S(O)_mR^{10}$,
  - i. $NR^{13}COR^{13}$,
  - j. $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, or
  - k. $C_{3-8}$cycloalkyl which is optionally partially unsaturated and optionally substituted by one or more oxo, halo, $OR^{13}$, $SR^{13}$, $C_{1-7}$alkyl, $CONH_2$ or $NR^{13}R^{13}$ substituents; or
  - l. pyrimidinyl, pyridyl, pyrrolyl, pyrazinyl, pyridazinyl, imidazolyl, or pyrazolyl;

each i is independently 2, 3, or 4;
each n is independently 1, 2, 3, 4 or 5;
each m is independently 1 or 2;
wherein any aryl other than G is optionally substituted with one or more $R^{15}$ substituents; and
wherein any het is optionally substituted with one or more =O, =N—$OR^{13}$, or $R^{15}$ substituents; or
a pharmaceutically acceptable salt thereof.

In another aspect, the present invention also provides:

a pharmaceutical composition comprising a compound of formula I, or a pharmaceutically acceptable salt thereof, and a pharmaceutically acceptable excipient (the composition preferably comprises an effective antiviral amount of the compound or salt);

a method of treating a herpesviral infection, comprising administering to a mammal (e.g. a human) in need of such treatment, a compound of formula I or a pharmaceutically acceptable salt thereof;

a method of treating atherosclerosis or restenosis comprising administering to a mammal (e.g. a human) in need of such treatment, a compound of formula I or a pharmaceutically acceptable salt thereof;

a method for inhibiting a viral DNA polymerase, comprising contacting (in vitro or in vivo) the polymerase with an effective inhibitory amount of a compound of formula I, or a pharmaceutically acceptable salt thereof.

a compound of formula I or a pharmaceutically acceptable salt thereof for use in medical treatment (e.g. the treatment of a herpesviral infection or the treatment of atherosclerosis or restenosis);

the use of a compound of formula I or a pharmaceutically acceptable salt thereof to prepare a medicament for treating a herpesviral infection in a mammal (e.g. a human);

the use of a compound of formula I or a pharmaceutically acceptable salt thereof to prepare a medicament for treating atherosclerosis or restenosis in a mammal (e.g. a human); and the use of a compound of formula I or a pharmaceutically acceptable salt thereof to prepare a medicament for inhibiting a viral DNA polymerase in a mammal (e.g. a human).

The invention also provides novel intermediates and processes disclosed herein that are useful for preparing compounds of formula I, including the generic and specific intermediates as well as the synthetic processes described in the Charts and Examples herein.

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Het" is a 4-16 membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S=O) and sulfonyl (S(=O)$_2$), or nitrogen, or an N-oxide thereof. Het includes "heteroaryl", which encompasses a radical attached via a ring carbon of a monocyclic aromatic ring containing five or six ring atoms consisting of carbon and 1, 2, 3, or 4 heteroatoms, such as non-peroxide oxygen (—O—), sulfur (—S—), oxygenated sulfur such as sulfinyl (S=O) and sulfonyl (S(=O)$_2$), or nitrogen N(X) wherein X is absent or is H, O, $C_{1-4}$alkyl, phenyl or benzyl, as well as a radical of an ortho-fused bicyclic heterocycle of about eight to ten ring atoms derived there from, particularly a benz-derivative or one derived by fusing a propylene, trimethylene, or tetramethylene diradical thereto. When heteroaryl is an ortho-fused benz-derivative it can be attached via any atom in an aromatic ring (e.g. an atom of the benz-ring).

"Partially unsaturated", for example, a $C_{1-7}$alkyl which is optionally partially unsaturated, means the named substituent has one or more unsaturations, such as one or more double bonds, one or more triple bonds, or both.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

"Mammal" denotes humans and animals. Animals specifically refer to, for example, food animals or companion animals.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. In particular, it is understood that compounds of formula I wherein $R^2$ is hydrogen can exist in the corresponding tautomeric "enol" form as illustrated in the following formula

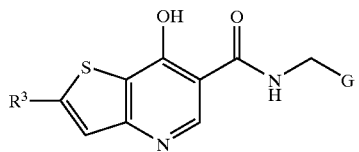

and that such tautomers are included as compounds of the invention.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, 'Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, $C_{1-7}$alkyl can be methyl, ethyl, propyl, isopropyl, butyl, iso-butyl, sec-butyl, pentyl, 3-pentyl, hexyl, or heptyl; $C_{3-8}$cycloalkyl can be cyclopropyl, cyclobutyl, cyclopentyl, cyclohexyl, cycloheptyl, or cyclooctyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-7}$alkanoyl can be acetyl, propanoyl, butanoyl, pentanoyl, 4-methylpentanoyl, hexanoyl, or heptanoyl; aryl can be phenyl, indenyl, or naphthyl.

"Heteroaryl" can be pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl,1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate or can include and their corresponding N-oxides as appropriate.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for "Het" is a four- (4), five- (5), six- (6), or seven- (7) membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S=O) and sulfonyl (S(=O)$_2$), or nitrogen, and which ring system is optionally fused to a benzene ring or an N-oxide thereof.

Another specific value for Het is a five- (5), six- (6), or seven- (7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic het diradical thereto.

Specific values of "het" are, but not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, azabicyclo[2.2.1]heptyl, and optionally their corresponding N-oxides.

A specific value for G is phenyl substituted with one $R^1$.

A more specific value for G is phenyl substituted with two $R^1$.

Another specific value for G is phenyl substituted with three $R^1$.

Another specific value for G is 4-chlorophenyl.
Another specific value for G is 4-fluorophenyl.
Another specific value for G is 3,4-dichlorophenyl.
Another specific value for G is 3,4-difluorophenyl.
Another specific value for G is 2,4-dichlorophenyl.
Another specific value for G is 2,4-difluorophenyl.
Another specific value for G is 4-chloro-2-fluorophenyl.
Another specific value for G is 2-chloro-4-fluorophenyl.
Another specific value for G is 3,4,5-trifluorophenyl.
Another specific value for G is 4-bromophenyl.
Another specific value for G is 4-methylphenyl.
Another specific value for G is 4-cyanophenyl.
Another specific value for G is 4-nitrophenyl.
A specific value for $R^1$ is F, Cl, or Br.
A more specific value for $R^1$ is Cl.
Another more specific value for $R^1$ is 4-Cl.
Another specific value for $R^1$ is methyl.
A specific value for $R^1$ is H.
Another specific value for $R^2$ is $C_{1-7}$alkyl which is optionally partially unsaturated and is optionally substituted with one or more $R^{11}$ substituents.
Another specific value for $R^2$ is methyl.
Another specific value for $R^2$ is ethyl.
A specific value for $R^3$ is H, halo, aryl, $S(O)_m R^6$, (C=O)$R^6$, (C=O)OH, (C=O)O$R^9$, cyano, $OR^{14}$, $NR^7R^8SR^{14}$, or $NHSO_2R^{12}$.

Another specific value for $R^3$ is $C_{1-7}$alkyl which is optionally partially unsaturated and optionally substituted with one or more $R^{11}$, $OR^{13}$, $SR^{10}$, $SR^{13}$, $NR^7R^8$, halo, $C_{1-7}$alkanoyl, and $SO_m R^9$ substituents.

A specific value for $R^3$ is $C_{1-7}$alkyl which is optionally partially unsaturated and optionally substituted with one or more $R^{11}$ substituents, or $C_{3-8}$cycloalkyl which is optionally partially unsaturated and optionally substituted by one or more $R^{11}$ or $C_{1-7}$alkyl substituents.

Another specific value for $R^3$ is $C_{1-7}$alkyl which is optionally partially unsaturated and optionally substituted with one or more $R^{11}$ substituents, or $C_{3-8}$cycloalkyl which is optionally partially unsaturated and optionally substituted by one or more $R^{11}$ or $C_{1-7}$alkyl substituents.

Another specific value for $R^3$ is (Z or E) —CH=CH(CH$_2$)$_n$R$_a$ or —C≡C(CH$_2$)$_n$R$_a$ wherein R$_a$ is $R^{11}$, $OR^{13}$, $SR^{10}$, $SR^{13}$, $NR^7R^8$, halo, $C_{1-7}$alkanoyl, or $SO_m R^9$.

Another specific value for $R^3$ is $CH_2NR^7R^8$.

A more specific value for $R^3$ is $CH_2NR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_m R^9$, $CONR^{13}R^{13}$, $CO_2R^{13}$, (C=O)$R^9$; het, aryl, cyano, or halo substituents.

Another specific value for $R^3$ is $CH_2NR^7R^8$ where $R^7$ is methyl, and $R^8$ is ethyl substituted with aryl or het, and an $OR^{14}$.

Another specific value for $R^3$ is $C_{1-7}$alkyl which comprises one double bond and is optionally substituted by one or more $R^{11}$ substituents.

Another specific value for $R^3$ is $C_{1-7}$alkyl which comprises one triple bond and is optionally substituted by one or more $R^{11}$ substituents.

Another specific value for $R^3$ is het, wherein the het is bound to the thieno ring via a carbon atom.

Another specific value for $R^3$ is het, wherein the het is bound to the thieno ring via a nitrogen atom.

Another specific value for $R^3$ is H.
Another specific value for $R^3$ is 3-hydroxy-propyn-1-yl.
Another specific value for $R^3$ is hydroxymethyl.
Another specific value for $R^3$ is N-methyl-N-{2-(4-hydroxyphenyl)-2-hydroxy-ethyl}aminomethyl.
Another specific value for $R^3$ is morpholinomethyl.
Another specific value for $R^3$ is N-methyl-N-{2-(3-hydroxyphenyl)-2-hydroxy-ethyl}aminomethyl.
Another specific value for $R^3$ is N-methyl-N-{2-(3-methoxyphenyl)-2-hydroxy-ethyl}aminomethyl.
Another specific value for $R^3$ is N-methyl-N-(2-furan-2-yl-2-hydroxy-ethyl) aminomethyl.
Another specific value for $R^3$ is N-methyl-N-{2-phenyl-2-hydroxy-ethyl}aminomethyl.
Another specific value for $R^3$ is N-methyl-N-{2-(1,3-thiazol-2-yl)ethyl}aminomethyl.
Another specific value for $R^3$ is N-methyl-N-{2-(4-methylsulfonylphenyl)-2-hydroxy-ethyl}aminomethyl.
Another specific value for $R^3$ is N-methyl-N-{2-(pyridin-2-yl)-2-hydroxy-ethyl}aminomethyl.
A specific value for $R^5$ is $(CH_2CH_2O)_tR^{10}$.
A specific value for $R^5$ is $C_{1-7}$alkyl which is optionally partially unsaturated and is optionally substituted by one or more $R^{11}$ substituents, or $C_{3-8}$cycloalkyl which is optionally partially unsaturated and optionally substituted by one or more $R^{11}$ or $C_{1-7}$alkyl substituents and optionally substituted with $R^{11}$.

A specific group of compounds are compounds of formula I wherein G is phenyl substituted with one or two $R^1$ groups when $R^2$ and $R^3$ are both $C_{1-7}$alkyl which $C_{1-7}$alkyl substituents are optionally partially unsaturated and optionally substituted with one or more $R^{11}$ substituents.

Another specific group of compounds are compounds of formula I wherein specific value for G is phenyl substituted at the 4-position with $R^1$ when $R^3$ is $C_{1-7}$alkyl which $C_{1-7}$alkyl is optionally substituted by $NR^7R^8$; and $R^2$ is $CH_3$.

Another specific value for G is 4-chlorophenyl when $R^3$ is $CH_2N(CH_3)CH_2CH(OH)$aryl or $CH_2N(CH_3)CH_2CH(OH)$het, and $R^2$ is $CH_3$.

A specific compound of the present invention is N-(4-Chlorobenzyl)-7-hydroxythieno[3,2-b]pyridine-6-carboxamide.

Another specific compound of the present invention is N-(4-Chlorobenzyl)-4-ethyl-7-oxo-4,7-dihydrothieno[3,2-b]pyridine-6-carboxamide.

Another specific compound of the present invention is N-(4-chlorobenzyl)-2-(3-hydroxyprop-1-ynyl)-4-methyl-7-oxo-4,7-dihydrothieno[3,2-b]pyridine-6-carboxamide.

Another specific compound of the present invention is N-(4-chlorobenzyl)-4-methyl-2-(morpholin-4-ylmethyl)-7-oxo-4,7-dihydrothieno[3,2-b]pyridine-6-carboxamide.

Another specific compound of the present invention is N-(4-chlorobenzyl)-2-{[[2-hydroxy-2-(3-methoxyphenyl)ethyl](methyl)amino]methyl}-4-methyl-7-oxo-4,7-dihydrothieno[3,2-b]pyridine-6-carboxamide.

Another specific compound of the present invention is N-(4-chlorobenzyl)-2-{[[2-(2-furyl)-2-hydroxyethyl](methyl)amino]methyl}-4-methyl-7-oxo-4,7-dihydrothieno[3,2-b]pyridine-6-carboxamide.

Another specific compound of the present invention is N-(4-chlorobenzyl)-2-{[(2-hydroxy-2-phenylethyl)(methyl)amino]methyl}-4-methyl-7-oxo-4,7-dihydrothieno[3,2-b]pyridine-6-carboxamide.

Another specific compound of the present invention is N-(4-chlorobenzyl)-2-{[[2-hydroxy-2-(1,3-thiazol-2-yl)ethyl](methyl)amino]methyl}-4-methyl-7-oxo-4,7-dihydrothieno[3,2-b]pyridine-6-carboxamide.

Another specific compound of the present invention is N-(4-chlorobenzyl)-2-{[{2-hydroxy-2-[4-(methylsulfonyl)

phenyl]ethyl}(methyl)amino]methyl}-4-methyl-7-oxo-4,7-dihydrothieno[3,2-b]pyridine-6-carboxamide.

Another specific compound of the present invention is N-(4-chlorobenzyl)-2-{[(2-hydroxy-2-pyridin-2-ylethyl)(methyl)amino]methyl}-4-methyl-7-oxo-4,7-dihydrothieno[3,2-b]pyridine-6-carboxamide.

A specific compound of the invention is a compound of formula I wherein: G is phenyl substituted with from one to five $R^1$ substituents;

each $R^1$ is independently
- (a) Cl,
- (b) Br,
- (c) F,
- (d) cyano,
- (e) $C_{1-7}$alkyl, or
- (f) $NO_2$;

$R^2$ is
- (a) H,
- (b) $R^5$,
- (c) $NR^7R^8$,
- (d) $SO_2R^9$, or
- (e) $OR^5$;

$R^3$ is
- (a) H,
- (b) halo,
- (c) aryl,
- (d) $S(O)_mR^6$,
- (e) $(C=O)R^6$,
- (f) $(C=O)OH$,
- (g) $(C=O)OR^9$,
- (h) cyano,
- (i) het, wherein the het is bound via a carbon atom,
- (j) $OR^{14}$,
- (k) $NR^7R^8$,
- (l) $SR^{14}$,
- (m) $NHSO_2R^{12}$,
- (n) $C_{1-7}$alkyl which is optionally partially unsaturated and optionally substituted by one or more $R^{11}$ substituents, or
- (o) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^5$ is
- (a) $(CH_2CH_2O)R^{10}$,
- (b) het, wherein the het is bound via a carbon atom,
- (c) aryl,
- (d) $C_{1-7}$alkyl which is optionally partially unsaturated and optionally substituted by one or more $R^{11}$ substituents, or
- (e) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^6$ is
- (a) $C_{1-7}$alkyl optionally substituted by aryl, het, $OR^{13}$, $SR^{13}$, $NR^{13}R^{13}$, halo, or $C_{3-8}$cycloalkyl, which $C_{3-8}$cycloalkyl is optionally substituted with $OR^{13}$,
- (b) $C_{3-8}$cycloalkyl which is optionally partially unsaturated and optionally substituted by one or more halo, $OR^{13}$, $SR^{13}$, or $NR^{13}R^{13}$ substituents,
- (c) $NR^7R^8$,
- (d) aryl, or
- (e) het, wherein the het is bound via a carbon atom;

$R^7$ and $R^8$ are independently
- (a) H,
- (b) aryl,
- (c) $C_{1-7}$alkyl which is optionally partially unsaturated and optionally substituted by one or more $NR^{13}R^{13}$, $OR^{14}$, $SR^{14}$, $S(O)_mR^9$, $P(=O)(OR^{14})(R^{14})$, $CONR^{13}R^{13}$, $CO_2R^{13}$, $(C=O)R^9$, het, aryl, cyano, or halo substituents,
- (d) $C_{3-8}$cycloalkyl which is optionally partially unsaturated and optionally substituted by one or more halo, $OR^{13}$, $SR^{13}$, oxo, or $NR^{13}R^{13}$ substituents,
- (e) $(C=O)R^9$, or
- (f) $R^7$ and $R^8$ together with the nitrogen to which they are attached form a het;

$R^9$ is
- (a) aryl,
- (b) het
- (c) $C_{3-8}$cycloalkyl, or
- (d) $C_{1-7}$alkyl which is optionally partially unsaturated and optionally substituted by one or more $NR^{13}R^{13}$, $OR^{14}$, $SR^{14}$, halo, $CONR^{13}R^{13}$, $CO_2R^{13}$, het, or aryl substituents;

$R^{10}$ is
- (a) H, or
- (b) $C_{1-7}$alkyl optionally substituted by OH;

$R^{11}$ is
- (a) $OR^{14}$,
- (b) $SR^{14}$,
- (c) $NR^7R^8$,
- (d) halo,
- (e) $CONH_2$,
- (f) $CONHR^9$,
- (g) $CONR^9R^9$,
- (h) $CO_2H$,
- (i) $CO_2R^9$,
- (j) het,
- (k) aryl,
- (l) cyano,
- (m) oxo,
- (n) $SO_mR^6$, or
- (o) $P(=O)(OR^{14})(R^{14})$;

$R^{12}$ is
- (a) H,
- (b) het,
- (c) aryl,
- (d) $C_{3-8}$cycloalkyl optionally substituted with $R^{11}$, or
- (e) $C_{1-7}$alkyl optionally substituted with $R^{11}$;

$R^{13}$ is
- (a) H, or
- (b) $C_{1-7}$alkyl;

$R^{14}$ is
- (a) H,
- (b) aryl,
- (c) het, wherein the het is bound through a carbon atom,
- (d) $C_{1-7}$alkyl which is optionally partially unsaturated and optionally substituted by aryl, het, $OR^{13}$, $SR^{13}$, $NR^{13}R^{13}$, halo, or $C_{3-8}$cycloalkyl which $C_{3-8}$cycloalkyl is optionally substituted by one or more $OR^{13}$, or
- (e) $C_{3-8}$cycloalkyl which is optionally partially unsaturated and optionally substituted by one or more halo, $OR^{13}$, $SR^{13}$, or $NR^{13}R^{13}$ substituents;

$R^{15}$ is
- (a) H,
- (b) halo,
- (c) $OR^{13}$, (d) $SR^{13}$,
(e) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $CO_2R^{13}$,
(l) $S(O)_mNR^{13}R^{13}$,
(m) $CONHR^{13}$,
(n) $C_{1-7}$alkyl which is optionally partially unsaturated and optionally substituted with oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, or
(o) $C_{3-8}$cycloalkyl which is optionally partially unsaturated and optionally substituted by one or more oxo, halo, $OR^{13}$, $SR^{13}$, $C_{1-7}$alkyl, $CONH_2$ or $NR^{13}R^{13}$ substituents;

each i is independently 2, 3, or 4;
each n is independently 1, 2, 3, 4 or 5;
each m is independently 1 or 2;
wherein any aryl other than G is optionally substituted with one or more $R^{15}$ substituents; and
wherein any het is optionally substituted with one or more $=O$, $=N-OR^{13}$, or $R^{15}$ substituents; or
a pharmaceutically acceptable salt thereof.

The present invention includes a pharmaceutically acceptable salt of any of the above mentioned compounds.

A specific compound of the invention is a compound of formula IV:

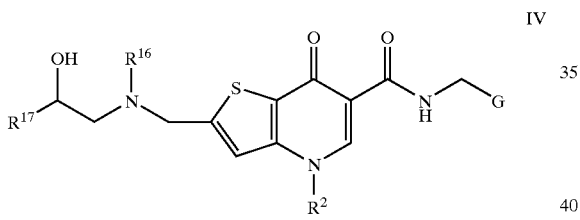

wherein:
R² and G have any of the values or specific values described herein;
$R^{16}$ is
(a) H,
(b) aryl,
(c) $C_{1-7}$alkyl which is optionally partially unsaturated and is optionally substituted by one or more $NR^{13}R^{13}$, $OR^{14}$, or $SR^{14}$, $S(O)_mR^9$, $CONR^{14}R^{14}$, $CO_2R^{13}$, (C=O)$R^9$, het, aryl, cyano, or halo substituents,
(d) $C_{3-8}$cycloalkyl which is optionally partially unsaturated and is optionally substituted by one or more halo, $OR^{13}$, $SR^{13}$, oxo, or $NR^{13}R^{13}$ substituents, or
(e) (C=O)$R^9$;
$R^{17}$ is
(a) aryl, or
(b) het;
$R^9$ is
(a) aryl,
(b) het
(c) $C_{3-8}$cycloalkyl, or
(d) $C_{1-7}$alkyl which is optionally partially unsaturated and optionally substituted by one or more $NR^{13}R^{13}$, $OR^{14}$, $SR^{14}$, halo, $CONR^{13}R^{13}$, $CO_2R^{13}$, het, or aryl substituents;

$R^{10}$ is
(a) H, or
(b) $C_{1-7}$alkyl optionally substituted by OH;
$R^{13}$ is
(a) H, or
(b) $C_{1-7}$alkyl;
$R^{14}$ is
(a) H,
(b) aryl,
(c) het,
(d) $C_{1-7}$alkyl which is optionally partially unsaturated and optionally substituted by aryl, het, $OR^{13}$, $SR^{13}$, $NR^{13}R^{13}$, halo, or $C_{3-8}$cycloalkyl which $C_{3-8}$cycloalkyl is optionally substituted by one or more $OR^{13}$, or
(e) $C_{3-8}$cycloalkyl which is optionally partially unsaturated and optionally substituted by one or more halo, $OR^{13}$, $SR^{13}$, or $NR^{13}R^{13}$ substituents; and
$R^{15}$ is
(a) H,
(b) halo,
(c) $OR^{13}$,
(d) $SR^{13}$,
(e) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $CO_2R^{13}$,
(l) $S(O)_mNR^{13}R^{13}$,
(m) $CONHR^{13}$,
(n) $S(O)_mR^{10}$,
(o) $NR^{13}COR^{13}$,
(p) $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, or
(q) $C_{3-8}$cycloalkyl which is optionally partially unsaturated and optionally substituted by one or more oxo, halo, $OR^{13}$, $SR^{13}$, $C_{1-7}$alkyl, $CONH_2$ or $NR^{13}R^{13}$ substituents; or
(r) pyrimidinyl, pyridyl, pyrrolyl, pyrazinyl, pyridazinyl, imidazolyl, or pyrazolyl;

each m is independently 1 or 2;
each n is independently 1, 2, 3, 4, or 5;
wherein any aryl other than G is optionally substituted with one or more $R^{15}$ substituents; and
wherein any het is optionally substituted with one or more $=O$, $=N-OR^{13}$, or $R^{15}$ substituents; or
a pharmaceutically acceptable salt thereof.

A specific compound of formula IV is a compound of formula V:

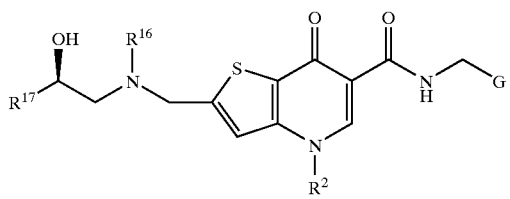

V or a pharmaceutically acceptable salt thereof.

Another specific compound of formula IV is a compound of formula VI:

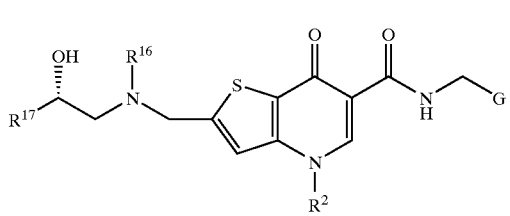

VI or a pharmaceutically acceptable salt thereof.

A more specific compound of the invention is a compound of formula IV wherein the hydroxy group has the same absolute configuration as the compound prepared at Example 21.

Specifically, the invention provides the synthetic processes and intermediates described in Preparations and Examples hereinbelow (e.g. Preparations 2, 3, 9, 13, 14, and 15).

The following Charts A–F describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts, by procedures analogous thereto, or by procedures which are known to one of ordinary skill in organic chemistry. All of the variables used in the charts are as defined below or as in the claims.

Ester A-1 (commercially available, e.g. from Acros-USA) can be saponified with aqueous sodium hydroxide and then acidified with acetic acid. The resulting 3-aminothiophene can be reacted with diethyl ethoxymethylenemalonate (DEEM) to afford aminomethylene malonate of the formula A-2. Refluxing in diphenyl ether induces cyclization to the compound of formula A-3. Reaction with excess strong base, such as lithium diisopropylamide (LDA), followed by quenching with a suitable polar solvent and a source of the formyl group, such as dimethylformamide (DMF), provides the carboxaldehyde of formula A-4. N-Alkylation with optionally substituted alkyl halides occurs in DMF in the presence of potassium carbonate to afford compounds of formula A-5. Reduction with sodium triacetoxyborohydride produces alcohols of the formula A-6, which are reacted with substituted benzylamines to afford amides of formula A-7. The alcohols can be converted to chlorides of formula A-8 by reaction with, for example, methanesulfonyl chloride (MsCl) in the presence of dimethylaminopyridine (DMAP). Displacement of the chloride with optionally substituted nucleophiles NuH, for example Nu=$R^{14}O$, $R^{14}S$ or $R^7R^8N$, in the presence of a suitable base yields compounds of the formula A-9.

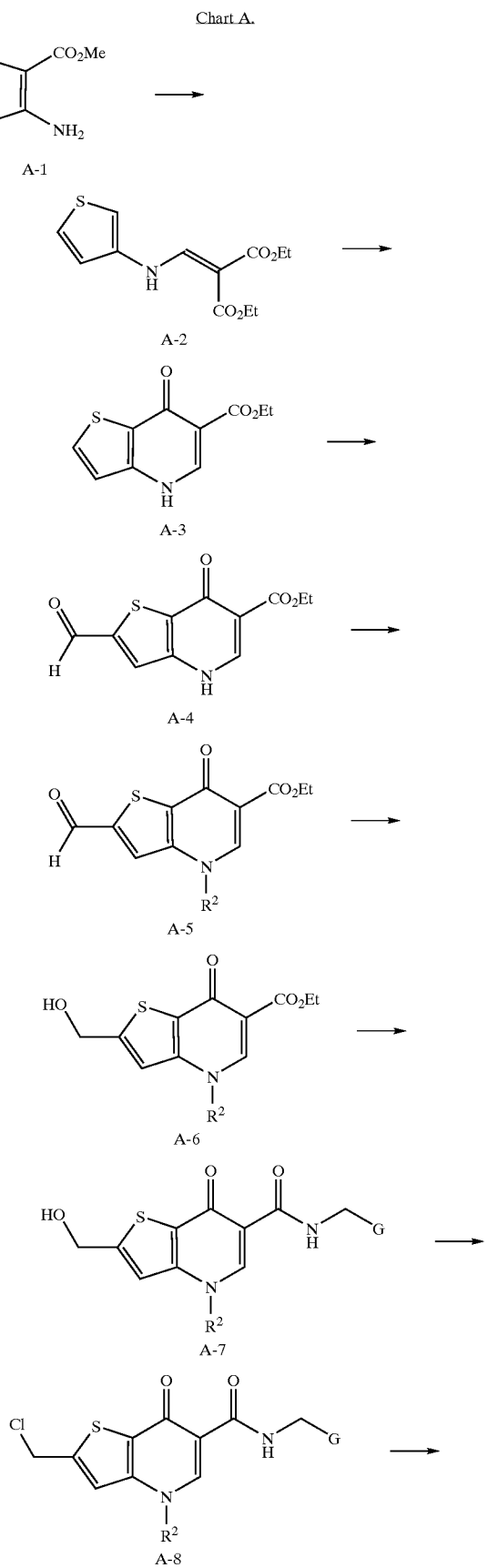

Chart A.

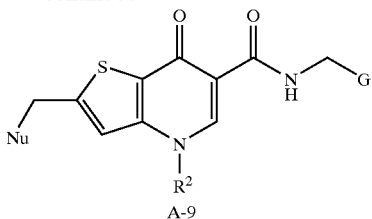

A-9

Specific compounds of this invention where R³ is hydrogen can be prepared as depicted in Chart B. Ethyl 7-hydroxythieno[3,2-b]pyridine-6-carboxylate (A-3) prepared as described in the literature (Elliott, R. L.; O'Hanlon, P. J.; Rogers, N. H. *Tetrahedron* 1987, 43, 3295–3302) is condensed with a benzylamine (e.g. 4-chlorobenzylamine, 4-bromobenzylamine, or 4-fluorobenzylamine) at high temperature, for example greater than about 50° C., to afford the corresponding compounds of the general formula B-2. Alternatively, ester A-3 is saponified to afford the corresponding acid which is then coupled with a benzylamine mediated by, for example 1,1'-carbonyldiimidazole or other suitable carboxylic acid activating agent, to likewise provide compounds of the general formula B-2. Amides of the formula B-2 can be alkylated at the ring nitrogen by treatment with an optionally substituted alkyl halide or alkyl mesylate in the presence of a base (e.g. potassium carbonate) or by reaction with an optionally substituted alkanol under Mitsunobu conditions to afford compounds of the general formula B-3 where R is a subset of R².

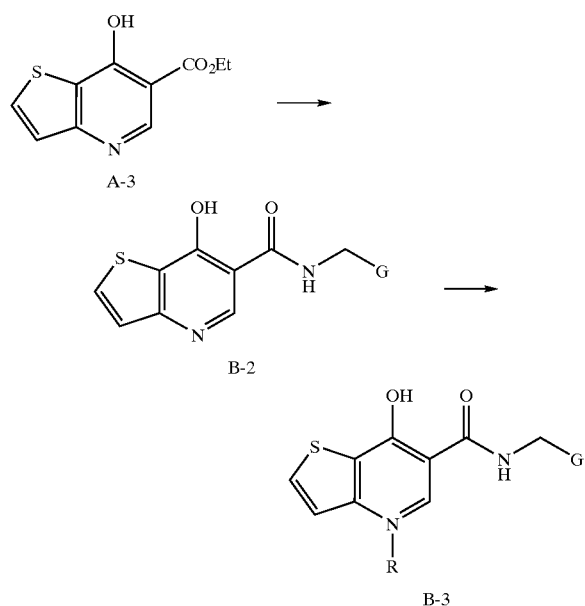

Iodination of thiophene A-3 with NIS and trifluoromethanesulfonic acid affords iodothiophene C-2. Condensation with a benzylamine (e.g. 4-chlorobenzylamine, 4-bromobenzylamine, or 4-fluorobenzylamine) at high temperature affords the corresponding amides of the general formula C-3. Amides of the formula C-3 are alkylated at the ring nitrogen by treatment with an optionally substituted alkyl halide or alkyl mesylate in the presence of a base (e.g. potassium carbonate) or by reaction with an optionally substituted alkanol under Mitsunobu conditions to afford compounds of the general formula C-4. Palladium catalyzed coupling of C-4 with alkynes leads to compounds of formula C-5 wherein A is for example $R^{11}$ as defined herein.

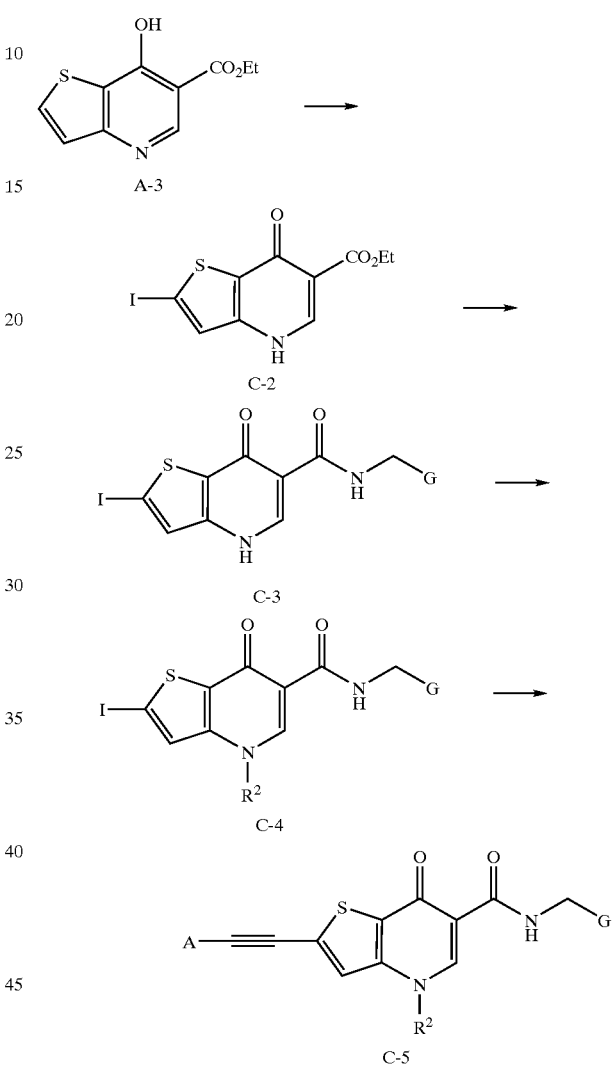

Amines of the formula D-3 can be prepared, for example, by bromination of ketones D-1 to form the corresponding bromoketones D-2, followed by reaction with a primary amine of the formula $R^7NH_2$, for example methylamine, and reduction with a suitable reducing agent, such as sodium borohydride to afford compounds of the formula D-3 wherein Y is aryl or het.

Chart D.

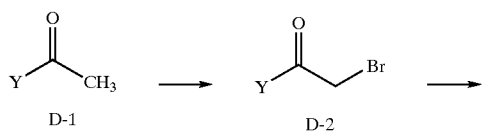

An alternative preparation of alcohols of the formula A-7 is presented in Chart E. Aldehyde A-4 is reduced with sodium borohydride to afford alcohol E-1. Reaction with substituted benzylamines affords amides of the formula E-2. N-Alkylation with optionally substituted alkyl halides occurs in DMF in the presence of potassium carbonate to afford compounds of the formula A-7.

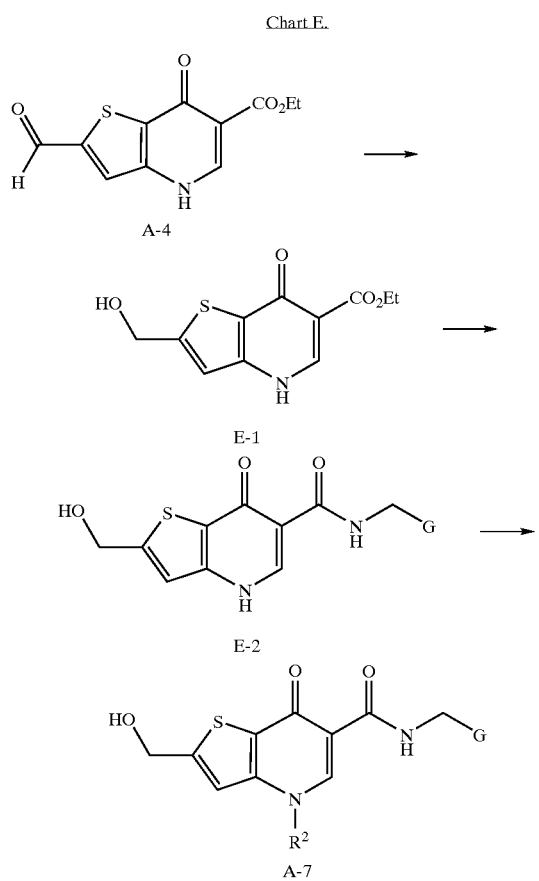

Chart E.

A-4

E-1

E-2

A-7

Amines of the formula F-6 can be prepared, for example, by conversion of ketones F-1 to enol silyl ethers of formula F-2 with triisopropylsilyl triflate and diisopropylethylamine. Chlorination with N-chlorosuccinimide, followed by hydrolysis with aqueous HF then can afford alpha-chloroketones of formula F-4. Reduction of the ketones can be accomplished with sodium borohydride and cerium trichloride to afford racemic alcohols of the formula F-5. Alternatively, the ketones F-4 can be reduced in an asymmetric fashion by, for example, hydrogenation with formic acid and the catalyst prepared from $[RuCl_2(\eta^6\text{-p-cymene})]_2$, $Et_3N$ and (1R, 2R)-N-p-toluenesulfonyl-1,2-diphenylethylenediamine to provide optically active alcohols of the formula F-5. Reaction of alcohols F-5 with methylamine then affords amines of formula F-6, wherein Y is aryl or het.

D-3

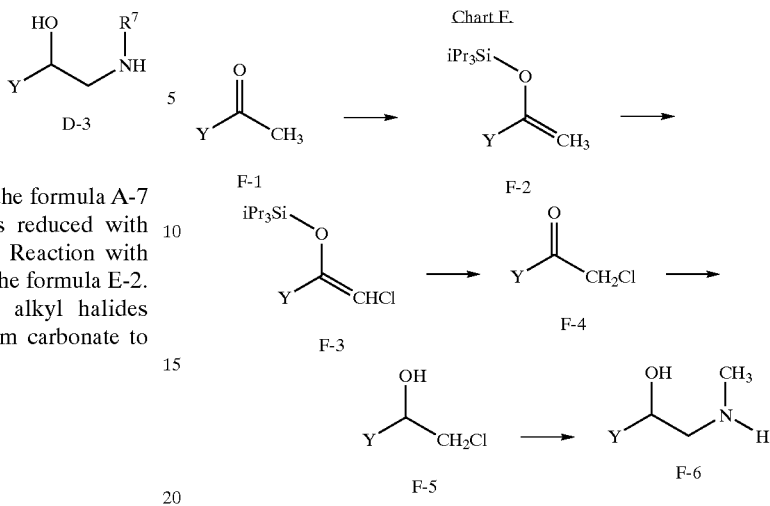

Chart E.

F-1

F-2

F-3

F-4

F-5

F-6

The invention also provides processes and intermediates described herein that are useful for preparing compounds of the invention. For example, compounds of the formula I wherein $R^2$ is other than H can be prepared from a corresponding compound of formula I wherein $R^2$ is H by, for example, alkylation. Accordingly, the present invention provides a method for preparing compounds of the formula I wherein $R^2$ is other than H, comprising alkylating a corresponding compound of the formula I wherein $R^2$ is hydrogen with a compound of the formula $R^2$-Z wherein Z is a suitable leaving group to provide the compound wherein $R^2$ is not H. Suitable Z leaving groups are known to those skilled in the art.

The invention also provides a method for preparing a compound of formula I:

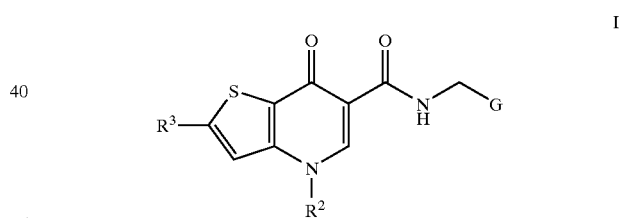

I wherein G and $R^2$ have the values described herein and $R^3$ is of the formula —$CH_2R^a$ where $R^a$ is, for example, $OR^{14}$, $SR^{14}$, $NR^7R^8$, N-linked Het, or CN, comprising: reacting a corresponding nucleophile with a compound of the formula III:

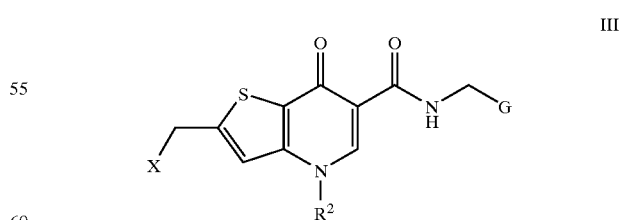

III wherein X is a leaving group, for example, Cl, Br, alkyl ester, anhydride, tosyl, mesyl, or like groups, under conditions suitable to provide the compound of formula I. Accordingly, the present invention provides a method for preparing compounds of the formula I wherein $R^3$ is $CH_2$-Nu where Nu is a nucleophile.

The invention also provides processes and intermediates described herein that are useful for preparing compounds of the invention. For example, the invention provides a method for preparing a compound of formula I wherein $R^2$ and $R^3$ have the values described herein comprising: reacting a nucleophile, for example, of the formula $NH_2$—$CH_2$—G with a compound of the formula II

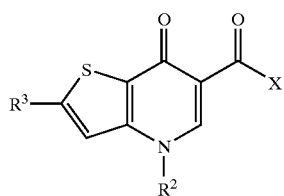

where X is a leaving group, for example, Cl, Br, alkyl ester, anhydride, tosyl, mesyl, or like groups, under conditions suitable to provide the compound of formula I. Suitable conditions for preparing an amide from a corresponding carboxylic acid are well known in the art. The reaction can be carried out under any suitable conditions. For example, the reaction can conveniently be carried out by activating a carboxylic acid of the formula C(=O)—OH with a suitable activating agent, and treating the activated acid of the formula C(=O)—X with, for example, a substituted benzyl amine or like reactants, to provide the compound of formula I. Suitable amines include, for example, 4-chlorobenzylamine, 4-fluorobenzylamine, 4-bromobenzylamine, 4-cyanobenzylamine, 4-nitrobenzylamine, and like amines. Accordingly, the present invention also provides intermediate compounds of the formula II wherein X is an activating leaving group.

The invention also provides a method for preparing a compound of formula A-4:

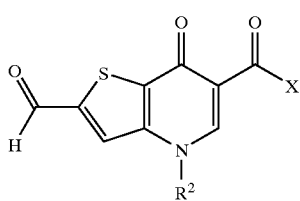

wherein $R^2$ is H, and X is a leaving group or blocking group, comprising: treating a compound of formula A-3:

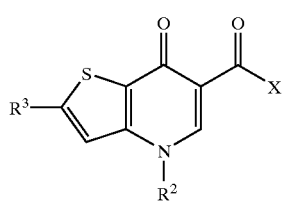

wherein $R^3$ is H, with a strong aprotic base and then reacting the resulting intermediate with a formylating agent.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metals, for example, sodium, potassium or lithium, or alkaline earth metal salts, for example calcium, of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally, for example, by intravenous, intraperitoneal or intramuscular injection, topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils.

Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1,000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1,000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 weight percent. The concentration in a semi-solid or solid composition such as a gel or a powder will be about 0.1–5 weight percent, preferably about 0.5–2.5 weight percent.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV). The compounds of the present invention may also be useful for the treatment of herpesvirus infections in animals, for example, illnesses caused by bovine herpesvirus 1–5 (BHV), ovine herpesvirus 1 and 2, Canine herpesvirus 1, equine herpesvirus 1–8 (EHV), feline herpesvirus 1 (FHV), and pseudorabies virus (PRV).

The compounds of the present invention may also useful for the treatment of several cardiovascular diseases such as atherosclerosis and restenosis. These diseases have been connected with inflammation of coronary vessel walls resulting from infection or reactivation of herpesviruses.

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM $MgCl_2$, 0.36 mg/mL BSA, and 90 nM $^3$H-dTTP. Assays are run with and without CHAPS, (3-[(3-cholamidopropyl)-dimethyl-ammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/mL BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 µL/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten µl of streptavidin-SPA beads (20 mg/mL in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Representative compounds of formula I that were tested were found to be active in this assay.

DESCRIPTION OF THE PREFERRED EMBODIMENTS

EXAMPLE 1

N-(4-Chlorobenzyl)-7-hydroxythieno[3,2-b]pyridine-6-carboxamide

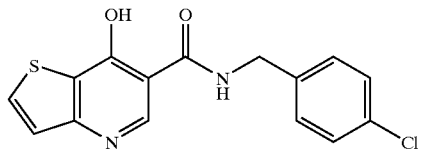

A mixture of ethyl 7-hydroxythieno[3,2-b]pyridine-6-carboxylate (223 mg) prepared as described in the literature (Elliott, R. L.; O'Hanlon, P. J.; Rogers, N. H. Tetrahedron 1987, 43, 3295–3302) and 4-chlorobenzylamine (1.2 mL) was heated to 190° C. for 1 h. The crude product was purified by column chromatography ($CH_2Cl_2$/methanol, 100/1; 50/1; 33/1) and the resulting solid was recrystallized from glacial acetic acid/water to afford 84 mg of the title compound as a tan solid.

Physical characteristics follow:

Mp 295° C. dec; $^1$H NMR (300 MHz, DMSO-$d_6$) δ 13.15, 10.44, 8.69, 8.13, 7.42–7.33, 4.54; $^{13}$C NMR (75 MHz, $CF_3CO_2D$) δ 160.7, 158.2, 138.5, 133.0, 130.7, 125.6, 124.3, 119.9, 116.9, 109.3, 97.1, 34.8; MS (ESI−) m/z 317 (M—H)$^-$. Anal. Found: C, 56.22; H, 3.43; N, 8.71; Cl, 10.80; S, 10.09.

EXAMPLE 2

N-(4-Chlorobenzyl)-4-ethyl-7-oxo-4,7-dihydrothieno[3,2-b]pyridine-6-carboxamide

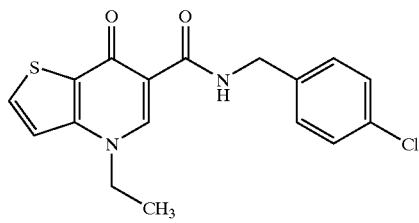

N-(4-chlorobenzyl)-7-hydroxythieno[3,2-b]pyridine-6-carboxamide (Example 1, 885 mg)was dissolved in DMF (20 mL) and to the solution was added potassium carbonate (1.92 g) and iodoethane (1.1 mL). The mixture was heated to 100° C. for 16 h. After cooling to room temperature, the reaction mixture was poured into water (100 mL) and extracted with EtOAc (3×100 mL). The combined organic layers were washed with water (3×25 mL) followed by brine (25 mL), dried ($MgSO_4$), and concentrated. The crude product was purified by column chromatography (EtOAc/heptane, 1/1; $CH_2Cl_2$/methanol, 100/1) and the resulting solid was recrystallized from ethanol to afford 590 mg of the title compound as a white solid.

Physical characteristics are as follows:

Mp 189–192° C.; $^1$H NMR (300 MHz, DMSO-$d_6$) δ 10.42, 8.76, 8.22, 7.65, 7.41–7.33, 4.54, 4.46, 1.39; $^{13}$C NMR (75 MHz, DMSO-$d_6$) δ 172.1, 164.8, 145.6, 144.7, 139.0, 135.5, 131.9, 131.1, 129.6, 128.8, 118.6, 112.7, 50.2, 41.9, 15.7; MS (EI) m/z 346 (M+). Anal. Found: C, 58.68; H, 4.47; N, 8.09; Cl, 10.26; S, 9.34.

Preparation 1

Ethyl 7-hydroxy-2-iodothieno[3,2-b]pyridine-6-carboxylate

To a stirring solution of ethyl 7-hydroxythieno[3,2-b]pyridine-6-carboxylate (Elliot, R. L, O'Hanlon, P. J., Rogers, N. H. Tetrahedron 43 (14) 3295–3302 (1987)) (2.50 g, 10.96 mmol) in trifluomethanesulfonic acid (50 mL) at 0° C. was added N-iodo succinimide (2.46 g, 10.96 mmol) portion wise. The mixture was stirred for 1 hour, allowing the solution to warm to ambient temperature. Ice (50 g) was added and the resulting aqueous extracted with $CH_2Cl_2$ (3×100 mL). The organic layers were combined, dried over $MgSO_4$ and solvent removed to afford 2.92 g title compound as a white solid.

Physical characteristics are as follows:

MS (EI) m/z (rel. intensity) 349 (M+, 0), 349 (98), 304 (17), 303 (99), 176 (18), 108 (27), 86 (13), 84 (17), 81 (23), 69 (22), 53 (21).

Preparation 2

N-(4-chlorobenzyl)-7-hydroxy-2-iodothieno [3,2-b]pyridine-6-carboxamide

A stirring mixture of ethyl 7-hydroxy-2-iodothieno[3,2-b]pyridine-6-carboxylate (1.5 g, 4.29 mmol) in 4-chlorobenzylamine (15 mL) was heated at 190° C. for 1 hour. The resulting dark solution was cooled to ambient temperature and 100 mL toluene added. The resulting solid was collected by filtration and dried at 50° C. for 16 h to afford 0.875 g title compound as a yellow solid.

Physical characteristics are as follows:

MS (EI) m/z (rel. intensity) 444 (M+, 0), 277 (37), 142 (27), 140 (99), 128 (21) 127 (54), 125 (88), 106 (23), 89 (20), 77 (27), 50 (21). Anal. Found: C, 40.76; H, 2.59; N, 6.35. The title compound is also a compound of formula I.

Preparation 3

N-(4-chlorobenzyl)-2-iodo-4-methyl-7-oxo-4,7-dihydrothieno[3,2-b]pyridine-6-carboxamide To a stirring mixture of N-(4-chlorobenzyl)-7-hydroxy-2-iodothieno[3,2-b]pyridine-6-carboxamide (0.50 g, 1.12 mmol) in DMF (20 mL) in a pressure tube was added $K_2CO_3$ (0.31 g, 2.25 mmol). To the resulting suspension was added $CH_3I$ (0.335g, 2.36 mmol), the vessel capped and heated at 90° C. for 16 h. The resulting dark suspension was cooled to ambient temperature and poured into $H_2O$ (100 mL). The aqueous solution was extracted with $CH_2Cl_2$ (3×100 mL). The organic layers were combined, dried over $MgSO_4$ and solvent removed to afford 0.38 g title compound as a yellow solid.

Physical characteristics are as follows:

MS (EI) m/z (rel. intensity) 458 (M+, 0), 458 (24), 291 (99), 192 (19), 165 (41), 140 (31), 138 (19), 137 (20), 136 (22), 128 (22), 127 (21). Anal. Found: C, 42.03; H, 2.74; N, 6.08. The title compound is also a compound of formula I.

EXAMPLE 3

N-(4-chlorobenzyl)-2-(3-hydroxyprop-1-ynyl)-4-methyl-7-oxo-4,7-dihydrothieno[3,2-b]pyridine-6-carboxamide

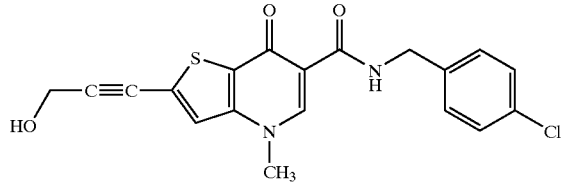

A mixture of N-(4-chlorobenzyl)-2-iodo-4-methyl-7-oxo-4,7-dihydrothieno[3,2-b]pyridine-6-carboxamide (0.20 g, 0.44 mmol), $Pd(PhCN)_2Cl_2$ (10 mg) CuI (7 mg) $Et_3N$ (1 mL) and propargyl alcohol (0.036 g, 0.66 mmol) in DMF was stirred at ambient temperature overnight. The solvent was removed and the residue partitioned between $H_2O$ and $CH_2Cl_2$ (100 mL each). The layers were shaken, the organic layer separated and dried over $MgSO_4$. The solvents were removed in vacuo and the residue purified via flash column chromatography (eluant 5% $MeOH/CH_2Cl_2$) to afford 0.117 g title compound as a white solid.

Physical characteristics are as follows:

MS (EI) m/z (rel. intensity) 386 (M+, 0), 219 (38), 86 (61), 84 (66), 78 (96), 65 (40), 64 (36), 63 (99), 62 (35), 61 (56), 51 (59). Anal. Calcd for $C_{19}H_{15}ClN_2O_3S(1.1\ H_2O)$. Found: C, 56.11; H, 3.90; N, 6.91.

Preparation 4

Diethyl 2-{[(thien-3-yl)amino]methylene}malonate

To a solution of methyl 3-amino-2-thiophenecarboxylate (Aldrich 23,290–4, 31.4 g, 0.20 mol) in 95% ethanol (180 mL) was added 1.0 N NaOH (240 mL). The mixture was heated to reflux and stirred for 1 hr. The resulting solution was cooled to room temperature before the addition of glacial acetic acid (13.8 mL, 0.24 mol). After stirring for 1.5 hrs at room temperature, diethyl ethoxymethylenemalonate (DEEM, 40.8 mL, 0.202 mol) was added. The mixture was stirred vigorously for 1 hr, and then it was left standing at room temp for 3 hours and filtered. The solid was collected and dried in a vacuum oven overnight at room temperature, affording a white solid (43.3 g).

Physical characteristics are as follows:

$^1$H NMR (DMSO-$d_6$) δ 10.78 (1 H), 8.29 (1 H), 7.58 (1 H), 7.39 (1 H), 7.28 (1 H), 4.15 (4 H), 1.24 (6 H); HPLC retention time (Conditions: Instrument: Hewlett Packard HP1100; Column: Zorbax SB-C18 (4.6×75 mm, 3.5 micron); Detector: UV @ 210 nm, 254 nm; Flow Rate: 2.0 mL/min; Gradient: 10:90 to 90:10 acetonitrile:0.07% aq. $H_3PO_4$ over 4.5 minutes; then 90:10 acetonitrile:0.07% aq. $H_3PO_4$ for 1.5 minutes)=3.80 min; MS (ESI+) for $C_{12}H_{15}NO_4S$ m/z 270 (M+H)+.

Preparation 5

Ethyl 7-hydroxythieno[3,2-b]pyridine-6-carboxylate

A solution of diethyl 2-{[(thien-3-yl)amino]methylene}malonate (43.4 g, 0.16 mol) in diphenyl ether (200 mL) in a 500 mL round bottom (RB) flask was degassed by three cycles of evacuation and nitrogen purge. The solution was then heated rapidly with a heating mantle to reflux and stirred at that temperature for 50 minutes. The heating mantle was removed and the yellow to brown solution was then stirred for 3 hours and was allowed to stand at room temperature for 16 hours, during which time a copious ppt appeared. The mixture was diluted with diethyl ether (300 mL) before collecting the solid by vacuum filtration. The collected solid was washed thoroughly with ether and dried in vacuo, leaving a white solid (21 g). More solid precipitated after the filtrate standing at room temperature overnight (7 g).

Physical characteristics are as follows:

$^1$H NMR (400 MHz, DMSO-$d_6$) δ 12.76 (1 H), 8.5 (1 H), 8.04 (1 H), 7.30 (1 H), 4.20 (2 H), 1.28 (3 H); HPLC ret time=0.572 min; MS (ESI+) for $C_{10}H_9NO_3S$ m/z 224 (M+H)+.

Preparation 6

Ethyl 2-formyl-7-oxo-4,7-dihydrothieno[3,2-b]pyridine-6-carboxylate

A fresh solution of LDA was prepared by adding n-BuLi (2.5 M in hexanes, 36 mL, 89 mmol) to a 0° C. solution of diisopropylamine (15 mL, 110 mmol) in anhyd. THF (100 mL). The LDA solution was then added via a needle cannula dropwise to a suspension of ethyl 7-hydroxythieno[3,2-b]pyridine-6-carboxylate (5.00 g, 22 mmol) in THF (200 mL) at −78° C. over a period of about 1 hr. After addition of the LDA, the solution was stirred at −78° C. for 1 hr before the dropwise addition of dry DMF (9 mL, 110 mmol). The reaction was stirred at −78° C. for 30 minutes and then the dry ice bath was removed. The temperature was allowed to rise to over 0° C. before the reaction was quenched by the addition of sat. aq. ammonium chloride (100 mL) and ice (50 g). Water (150 mL) was added, and the mixture was stirred vigorously for 30 minutes. The solid ppt was collected by vacuum filtration, and the solid was washed with water. Drying in vacuo left a yellow solid (5.22 g).

Physical characteristics are as follows:

$^1$H NMR (400 MHz, DMSO-$d_6$) δ 10.07 (1 H), 8.68 (1 H), 8.16 (1 H), 4.23 (2 H), 1.30 (3 H); HPLC ret time=1.709 min; MS (ESI+) for $C_{11}H_9NO_4S$ m/z 252 (M+H)+.

Preparation 7
Ethyl 2-formyl-4-methyl-7-oxo-4,7-dihydrothieno[3,2-b]pyridine-6-carboxylate Methyl iodide (1.2 mL, 19.3 mmol) was added to a mixture of ethyl 2-formyl-7-oxo-4,7-dihydrothieno[3,2-b]pyridine-6-carboxylate (3.0 g, 11.9 mmol), potassium carbonate (2.5 g, 18.1 mmol) in DMF (30 mL) at 0° C. After the addition of methyl iodide, the mixture was stirred at room temperature for 1 hr. The mixture was diluted with water (40 mL), stirred at room temperature for 15 minutes, and then filtered. The collected solid was washed with water and dried in vacuo, leaving a solid (1.3 g, 41%). The aqueous phase was extracted with methylene chloride (2×50 mL). The organic layers were combined, washed with water (50 mL) and brine (50 mL), and dried over magnesium sulfate. Removal of the solvent gave a second crop of product (0.34 g).

Physical characteristics are as follows:
$^1$H NMR (400 MHz, DMSO-$d_6$) δ 10.10 (1 H), 8.66 (1 H), 8.43 (1 H), 4.24 (2 H), 4.00 (3 H), 1.28 (3 H); $^{13}$C NMR (DMSO-d6) δ 185.54, 169.32, 164.14, 148.79, 145.47, 143.65, 135.80, 127.57, 111.74, 59.96, 41.25, 14.18; HPLC ret time=1.827 min; MS (ESI+) for $C_{12}H_{11}NO_4S$ m/z 266 (M+H)$^+$.

Preparation 8
Ethyl 2-(hydroxymethyl)-4-methyl-7-oxo-4,7-dihydrothieno[3,2-b]pyridine-6-carboxylate To a solution of ethyl 2-formyl-4-methyl-7-oxo-4,7-dihydrothieno[3,2-b]pyridine-6-carboxylate (1.0 g, 3.8 mmol) in 1,2-dichloroethane (23 mL) was added sodium triacetoxyborohydride (1.6 g, 7.5 mmol). The reaction was stirred at room temperature for 24 hours. The reaction was poured into sat. aq. sodium bicarbonate (50 mL) and methylene chloride (30 mL), before it was quenched with water (50 mL). The mixture was allowed to stand at 0° C. overnight. The solid ppt. was collected by vacuum filtration and washed with water. Drying in vacuo yielded an off-white solid (0.36 g, 36%). The filtrate was concentrated to near dryness and diluted with water (20 mL). Filtration followed by treatment with high vacuum gave a second crop of product (0.45 g).

Physical characteristics are as follows:
$^1$H NMR (400 MHz, DMSO-$d_6$) δ 8.48 (1 H), 7.32 (1 H), 5.88 (1 H), 4.74 (2 H), 4.21 (2 H), 3.90 (3 H), 1.27 (3 H); HPLC ret time=1.522 min; MS (ESI+) for $C_{12}H_{13}NO_4S$ m/z 268 (M+H)$^+$.

EXAMPLE 4

N-(4-chlorobenzyl)-2-(hydroxymethyl)-4-methyl-7-oxo-4,7-dihydrothieno[3,2-b]pyridine-6-carboxamide

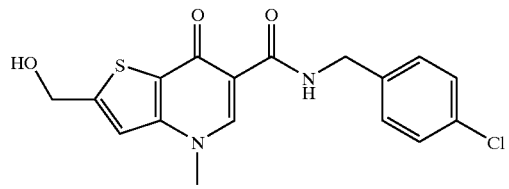

Ethyl 2-(hydroxymethyl)-4-methyl-7-oxo-4,7-dihydrothieno[3,2-b]pyridine-6-carboxylate (250 mg, 0.94 mmol) was suspended in 4-chlorobenzylamine (2.0 mL, 16.4 mmol). The mixture was stirred at 80° C. for 16 hours before it was quenched with a mixture of 1.0 M hydrochloric acid (25 mL) and ice (5 g). The mixture was stirred at room temperature for 1 hr. The solid ppt. was collected by vacuum filtration and washed thoroughly with 50 mL of water. Drying in vacuo left a white solid (0.26 g).

Physical characteristics are as follows:
$^1$H NMR (400 MHz, DMSO-$d_6$) δ 10.46 (1 H), 8.68 (1 H), 7.40, 7.37 (4 H), 5.94 (1 H), 4.78 (2 H), 4.54 (2 H), 3.99 (3 H); HPLC ret time=2.763 min; MS (ESI+) for $C_{17}H_{15}ClN_2O_3S$ m/z 363 (M+H)$^+$.

Preparation 9
N-(4-chlorobenzyl)-2-(chloromethyl)-4-methyl-7-oxo-4,7-dihydrothieno[3,2-b]pyridine-6-carboxamide Methanesulfonyl chloride (0.22 mL, 2.8 mmol) was added to a mixture of ethyl 2-(hydroxymethyl)-4-methyl-7-oxo-4,7-dihydrothieno[3,2-b]pyridine-6-carboxylate (400 mg, 1.1 mmol), collidine (0.37 mL, 2.8 mmol) and DMAP (67 mg, 0.55 mmol) in DMF (20 mL). The reaction was stirred at room temperature for 2 hours, going to an orange/amber solution. The reaction mixture was poured into ice water (40 mL of water +50 g of ice) and stirred for 10 minutes. The solid ppt was collected by filtration, washed with water and dried in vacuo, leaving the title compound as a white solid (0.36 g). Physical characteristics are as follows: $^1$H NMR (400 MHz, DMSO-$d_6$) δ 10.3 (1 H), 8.72 (1 H), 7.40, 7.37 (4 H), 5.16 (2 H), 4.54 (2 H), 4.01 (3 H); HPLC ret time=3.66 min; MS (ESI+) for $C_{17}H_{14}Cl_2N_2O_2S$ m/z 381 (M+H)$^+$. The title compound is also a compound of formula I.

EXAMPLE 5

N-(4-chlorobenzyl)-4-methyl-2-(morpholin-4-ylmethyl)-7-oxo-4,7-dihydrothieno [3,2-b]pyridine-6-carboxamide

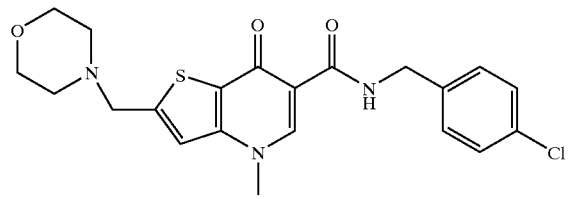

A mixture of N-(4-chlorobenzyl)-2-(chloromethyl)-4-methyl-7-oxo-4,7-dihydrothieno[3,2-b]pyridine-6-carboxamide (50 mg, 0.13 mmol), morpholine (17.4 mg, 0.20 mmol) and diisopropylethylamine (35 μL, 0.20 mmol) in dry DMF (2.7 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (48 mg) as a flocculent white solid.

Physical characteristics are as follows: $^1$H NMR (400 MHz, DMSO-$d_6$) δ 10.46 (1 H), 8.67 (1 H), 7.47 (1 H), 7.34 (4 H), 4.54 (2 H), 3.99 (3 H), 3.81 (2 H), 3.61 (4 H), 2.47 (4 H); HPLC ret time=2.224 min; Anal. Found: C, 58.35; H, 5.15; N, 9.37; MS (ESI+) m/z 432 (M+H)$^+$.

EXAMPLE 6

N-(4-chlorobenzyl)-2-{[[2-hydroxy-2-(3-methoxyphenyl)ethyl](methyl)amino]methyl}-4-methyl-7-oxo-4,7-dihydrothieno[3,2-b]pyridine-6-carboxamide

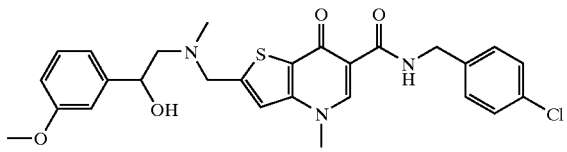

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 1-(3-methoxyphenyl)-2-(methylamino)ethanol (Chem.Abstr.; 1957; 6548) (36 mg, 0.20 mmol) and diisopropylethylamine (35 μL, 0.20 mmol) in dry DMF (2.7 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (47 mg) as a white solid.

Physical characteristics are as follows: HPLC ret time= 2.639 min; MS (ESI+) m/z 526 (M+H)$^+$.

Preparation 10

2-bromo-1-(2-furyl)ethanone

Bromine (6.5 mL, 127 mmol) was added dropwise over 1 hour to a solution of 2-acetylfuran (11.0 g, 100 mmol) in dioxane/Et$_2$O (1/2, 60 mL) at 0° C. After addition was complete, the reaction was warmed to room temperature and stirred for 2 hours. A saturated ammonium chloride solution (70 mL) was then added. The organic layer was removed and the aqueous layer was extracted with Et$_2$O (2×50 mL). The combined organic layers were dried over MgSO$_4$, filtered, and concentrated. The resulting brown solid was purified using a Biotage 40 M column (hexanes/CH$_2$Cl$_2$, 70/30) to yield the bromoketone as a yellow oil that solidified upon standing (4.40 g).

Physical characteristics are as follows:
$^1$H NMR (DMSO-d$_6$) δ 4.66 (2 H), 6.78 (1 H), 7.66 (1 H), 8.09 (1 H).

Preparation 11

1-(2-furyl)-2-(methylamino)ethanol

A solution of 2-bromo-1-(2-furyl)ethanone (3.0 g, 15.88 mmol) in methanol (16 mL) was added dropwise to a 2.0 M solution of methylamine in methanol (79.4 mL, 158.8 mmol) at 0° C. The reaction stirred at 0° C. for 30 minutes. A solution of sodium borohydride (0.90 g, 23.82 mmol) in H$_2$O (16 mL) was then added dropwise. The reaction mixture was stirred at 0° C. for 30 minutes and then quenched with 2 N HCl (to pH 3-4). The reaction mixture was concentrated in vacuo to remove methanol and then poured into a cold mixture of EtOAc (80 mL) and 2 N HCl (40 mL). The organic layer was removed. The aqueous layer was adjusted to pH 12 with 2 N NaOH and extracted with EtOAc (3×80 mL). The combined extracts were dried over MgSO$_4$, filtered, and concentrated in vacuo. The resulting brown oil was purified using a Biotage 40 M column (CHCl$_3$/methanol, 95/5; CHCl$_3$/methanol/NH4OH, 90/10/1) to yield the aminoalcohol as a brown oil (0.86 g).

Physical characteristics are as follows:
$^1$H NMR (DMSO-d$_6$) δ 2.33 (3 H), 2.77-2.66 (2 H), 4.61 (1 H), 6.26 (1 H), 6.38 (1 H), 7.56 (1 H). OAMS (ES+) m/z 141.9 (M+H)$^+$.

EXAMPLE 7

N-(4-chlorobenzyl)-2-{[[2-(2-furyl)-2-hydroxyethyl](methyl)amino]methyl}-4-methyl-7-oxo-4,7-dihydrothieno[3,2-b]pyridine-6-carboxamide

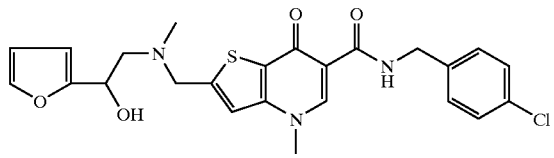

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 1-(2-furyl)-2-(methylamino)ethanol (Preparation 11) (28 mg, 0.20 mmol) and diisopropylethylamine (35 μL, 0.20 mmol) in dry DMF (2.7 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (49 mg) as a white solid.

Physical characteristics are as follows: HPLC ret time= 2.414 min; Anal. Found: C, 56.23; H, 4.82; N, 8.11; MS (ESI−) m/z 484 (M—H)$^+$.

EXAMPLE 8

N-(4-chlorobenzyl)-2-{[(2-hydroxy-2-phenylethyl)(methyl)amino]methyl}-4-methyl-7-oxo-4,7-dihydrothieno[3,2-b]pyridine-6-carboxamide

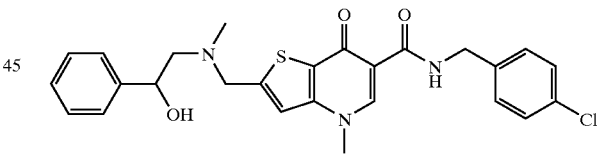

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 2-(methylamino)-1-phenylethanol (Aldrich, 30 mg, 0.20 mmol) and diisopropylethylamine (35 μL, 0.20 mmol) in dry DMF (2.7 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (47 mg) as a white solid.

Physical characteristics are as follows: HPLC ret time= 2.595 min; Anal. Found: C, 59.15; H, 5.26; N, 7.96; MS (ESI+) m/z 496 (M+H)$^+$.

EXAMPLE 9

N-(4-chlorobenzyl)-2-{[[2-hydroxy-2-(1,3-thiazol-2-yl)ethyl](methyl)amino]methyl}-4-methyl-7-oxo-4,7-dihydrothieno [3,2-b]pyridine-6-carboxamide

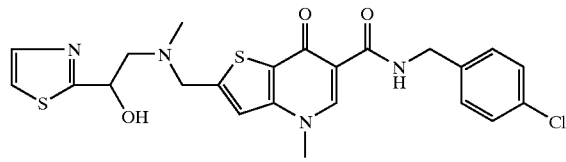

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 2-(methylamino)-1-(1,3-thiazol-2-yl)ethanol (prepared from 2-acetyl-1,3-thiazole by the procedure outlined in Preparation 10 and 11)(31 mg, 0.20 mmol) and diisopropylethylamine (35 μL, 0.20 mmol) in dry DMF (2.7 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (39 mg) as a flocculent white solid.

Physical characteristics are as follows: HPLC ret time= 2.357 min; Anal. Found: C, 53.82; H, 4.62; N, 10.72; MS (ESI+) m/z 503 (M+H)+.

EXAMPLE 10

N-(4-chlorobenzyl)-2-{[{2-hydroxy-2-[4-(methylsulfonyl)phenyl]ethyl}(methyl)amino]methyl}-4-methyl-7-oxo-4,7-dihydrothieno[3,2-b]pyridine-6-carboxamide

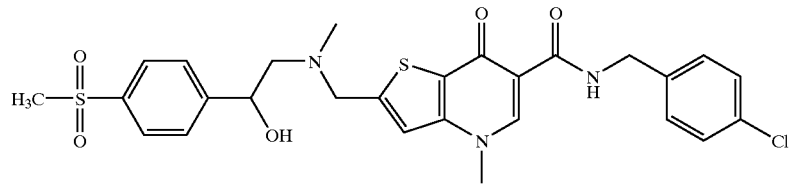

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 2-(methylamino)-1-[4-(methylsulfonyl)phenyl]ethanol (prepared from 4-methylsulphonylacetophenone by the procedure outlined in Preparation 10 and 11)(46 mg, 0.20 mmol) and diisopropylethylamine (35 μL, 0.20 mmol) in dry DMF (2.7 mL) was heated to 60° C., becoming a solution. The reaction was stirred for 4 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (54 mg) as a flocculent white solid.

Physical characteristics are as follows: HPLC ret time= 2.416 min; MS (ESI+) m/z 574 (M+H)+.

EXAMPLE 11

N-(4-chlorobenzyl)-2-{[(2-hydroxy-2-pyridin-2-ylethyl)(methyl)amino]methyl}-4-methyl-7-oxo-4,7-dihydrothieno [3,2-b]pyridine-6-carboxamide

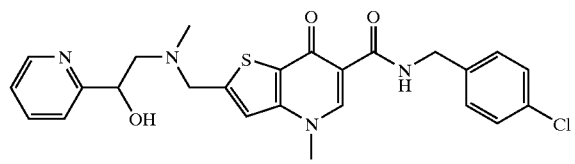

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 2-(methylamino)-1-pyridin-2-ylethanol (prepared from 2-acetylpyridine by the procedure outlined in Preparation 10 and 11)(31 mg, 0.20 mmol) and diisopropylethylamine (35 μL, 0.20 mmol) in dry DMF (2.7 mL) was heated to 60° C., becoming a solution. The reaction was stirred for 4 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (45 mg) as a flocculent white solid.

Physical characteristics are as follows: HPLC ret time= 2.228 min; MS (ESI+) m/z 519 (M+Na)+.

EXAMPLE 12

N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide

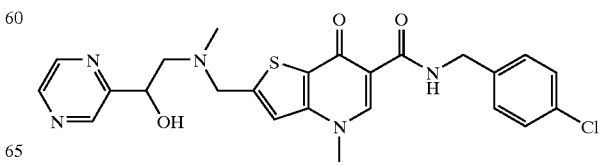

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 2-(methylamino)-1-pyrazin-2-ylethanol (prepared from 2-acetylpyrazine by the procedure outlined in Preparations 10 and 11)(0.20 mmol) and diisopropylethylamine (35 μL, 0.20 mmol) in dry DMF (2.7 mL) was heated to 60° C., becoming a solution. The reaction was stirred for 4 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (23 mg).

Physical characteristics are as follows:
HPLC ret time=2.21 min; MS (ESI+) m/z 498 (M+H)+.

EXAMPLE 13

N-(4-chlorobenzyl)-2-{[[2-(5-cyanothien-2-yl)-2-hydroxyethyl](methyl)amino]methyl}-4-methyl-7-oxo-4,7-dihydrothieno[3,2-b]pyridine-6-carboxamide

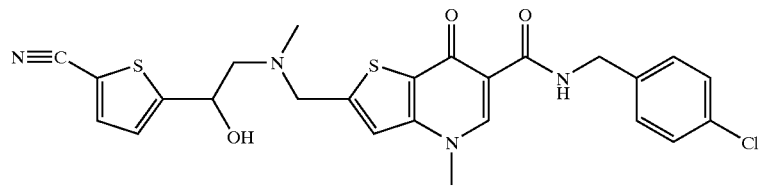

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), 5-[1-hydroxy-2-(methylamino)ethyl]thiophene-2-carbonitrile (prepared from 5-acetylthiophene-2-carbonitrile by the procedure outlined in Preparations 10 and 11)(0.20 mmol) and diisopropylethylamine (35 μL, 0.20 mmol) in dry DMF (2.7 mL) was heated to 60° C., becoming a solution. The reaction was stirred for 4 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (37 mg).

Physical characteristics are as follows:

HPLC ret time=2.60 min; MS (ESI+) m/z 527 (M+H)+.

EXAMPLE 14

N-(4-chlorobenzyl)-2-{[[2-hydroxy-2-(4-hydroxyphenyl)ethyl](methyl)amino]methyl}-4-methyl-7-oxo-4,7-dihydrothieno[3,2-b]pyridine-6-carboxamide

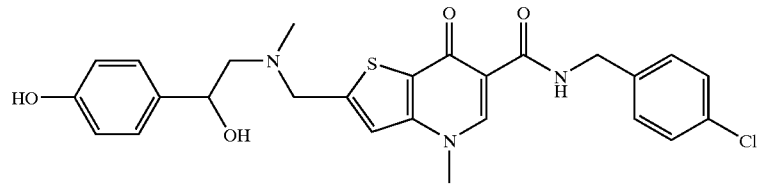

A mixture of N-(4-chlorobenzyl)-2-(chloromethyl)-4-dimethyl-7-oxo-4,7-dihydrothieno[3,2-b]pyridine-6-carboxamide (50 mg, 0.13 mmol), synephrine (0.20 mmol) and diisopropylethylamine (35 μL, 0.20 mmol) in dry DMF (2.7 mL) was heated to 60° C., becoming a solution. The reaction was stirred for 4 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL) gave the title compound (38 mg).

Physical characteristics are as follows:
HPLC ret time=2.34 min; MS (ESI+) m/z 512 (M+H)+.

Preparation 12
Ethyl 2-(hydroxymethyl)-7-oxo-4,7-dihydrothieno[3,2-b]pyridine-6-carboxylate To a 0° C. mixture of ethyl 2-formyl-7-oxo-4,7-dihydrothieno[3,2-b]pyridine-6-carboxylate (Preparation 6, 0.628 g, 2.5 mmol) and acetic acid (0.71 mL, 12.5 mmol) in 1,2-dichloroethane (23 mL) was added sodium triacetoxyborohydride (1.06 g, 5.0 mmol). The mixture was stirred at 0° C. for 5 minutes and at room temperature for 24 hrs. A saturated solution of sodium bicarbonate (25 mL) and methylene chloride (25 mL) were added. After stirring vigorously for 5 minutes, the mixture was filtered. The collected solid was washed with water and methylene chloride, then dried in vacuo, leaving the title compound as a pale yellow solid (0.486 g).

Physical characteristics are as follows:
$^1$H NMR (400 MHz, DMSO-$d_6$) δ 12.6 (1H), 8.44 (1 H), 7.13 (1 H), 5.19 (1H), 4.71 (2H), 4.20 (2H), 1.27 (3H); HPLC ret time=1.39 min; MS (ESI−) for $C_{11}H_{11}NO_4S$ m/z 252 (M−H)−.

Preparation 13
N-(4-chlorobenzyl)-2-(hydroxymethyl)-7-oxo-4,7-dihydrothieno[3,2-b]pyridine-6-carboxamide A mixture of ethyl 2-(hydroxymethyl)-7-oxo-4,7-dihydrothieno[3,2-b]pyridine-6-carboxylate (1.40 g, 5.53 mmol) in 4-chlorobenzylamine (13.5 mL, 111 mmol) under nitrogen was heated at 80° C. for 5 hrs. The reaction was cooled to room temperature before the addition of 1 N HCl (120 mL). The resulting pale yellow precipitate was collected by filtration and washed thoroughly with 1 N HCl, then water. Drying in vacuo left the title compound as a pale yellow solid (1.85 g).

Physical characteristics are as follows:

$^1$H NMR (400 MHz, DMSO-d$_6$) δ) 13.1 (1H), 10.45 (1H), 8.64 (1H), 7.37 (4H), 7.20 (1 H), 4.75 (2H), 4.54 (2H); HPLC ret time=2.65 min; MS (ES−) m/z 347. The title compound is also a compound of formula I.

Preparation 14

N-(4-chlorobenzyl)-2-(hydroxymethyl)-4-{2-[methoxy (methyl)amino]-2-oxoethyl}-7-oxo-4,7-dihydrothieno[3,2-b]pyridine-6-carboxamide A mixture of N-(4-chlorobenzyl)-2-(hydroxymethyl)-7-oxo-4,7-dihydrothieno[3,2-b]pyridine-6-carboxamide (100 mg, 0.288 mmol), potassium carbonate (60 mg, 0.43 mmol) and 2-chloro-N-methoxy-N-methylacetamide (200 mg) in DMF (1.5 mL) was shaken at room temp. for 48 hrs. The mixture was diluted with water (5 mL), and the resulting solid was collected by filtration. The crude solid was recrystallized from aq. ethanol to afford title compound (90 mg). The title compound is also a compound of formula I.

Physical characteristics are as follows:

$^1$H NMR (400 MHz, DMSO-d$_6$) δ) 10.45 (1H), 8.73 (1H), 7.37 (4H); 7.26 (1H), 5.91 (1H), 5.47 (2H), 4.74 (2H), 4.54 (2H), 3.86 (3H), 3.16 (3 H); HPLC ret time=2.86 min; MS (ES+) m/z 450, 452.

Preparation 15

N-(4-chlorobenzyl)-2-(chloromethyl)-4-{2-[methoxy (methyl)amino]-2-oxoethyl}-7-oxo-4,7-dihydrothieno [3,2-b]pyridine-6-carboxamide To a mixture of N-(4-chlorobenzyl)-2-(hydroxymethyl)-4-{2-[methoxy(methyl)amino]-2-oxoethyl}-7-oxo-4,7-dihydrothieno [3,2-b]pyridine-6-carboxamide (80 mg, 0.18 mmol), collidine (59 μL, 0.44 mmol) and DMAP (3.2 mg) in DMF (2.6 mL) was added methanesulfonyl chloride (35 μL, 0.44 mmol). The reaction was stirred at room temperature for 24 hrs, then cooled to 0° C. before the addition of water (5 mL). The resulting ppt was collected by filtration and washed with water and dried in vacuo, leaving the title compound as an off-white solid (80 mg). The title compound is also a compound of formula I.

Physical characteristics are as follows:

$^1$H NMR (400 MHz, DMSO-d$_6$) δ) 10.3 (1H), 8.78 (1 H), 7.54 (1H), 7.38 (4H), 5.50 (2H), 5.12 (2H), 4.55 (2H), 3.86 (3H), 3.17 (3H); HPLC ret time=3.69 min.; MS (ES+) m/z 468, 470.

EXAMPLE 15

N-(4-chlorobenzyl)-2-{[[2-(2-furyl)-2-hydroxyethyl] (methyl)amino]methyl}-4-{2-[methoxy(methyl) amino]-2-oxoethyl}-7-oxo-4,7-dihydrothieno[3,2-b] pyridine-6-carboxamide

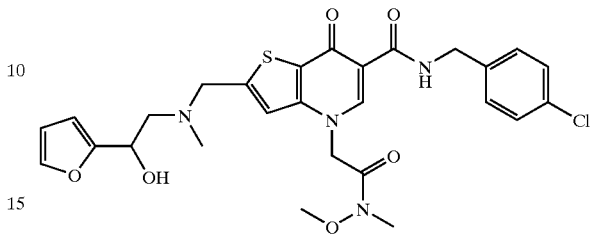

Diisopropylethylamine (34 μL, 0.19 mmol) was added to a mixture of N-(4-chlorobenzyl)-2-(chloromethyl)-4-{2-[methoxy(methyl)amino]-2-oxoethyl}-7-oxo-4,7-dihydrothieno[3,2-b]pyridine-6-carboxamide (60 mg, 0.13 mmol) and 1-(2-furyl)-2-(methylamino)ethanol (27 mg, 0.19 mmol) in DMF (2.0 mL). The mixture was shaken at 60° C. for 3 hrs. The reaction was cooled to room temperature before the addition of water (5 mL). The resulting ppt was collected by filtration and washed with water. After drying in vacuo, the title compound was obtained as a pale yellow solid (41 mg).

Physical characteristics are as follows:

$^1$H NMR (400 MHz, DMSO-d$_6$) δ) 10.45 (1H), 8.71 (1H), 7.56 (1H), 7.37 (4H), 7.28 (1H), 6.39 (1H), 6.29 (1H), 5.45 (2H), 5.31 (1H), 4.55 (2H), 3.85 (5H), 3.16 (3H), 2.76 (2H), 2.27 (3H); HPLC ret time=2.51 min; MS (ES+) m/z 573, 575.

EXAMPLE 16

N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide (enantiomer B)

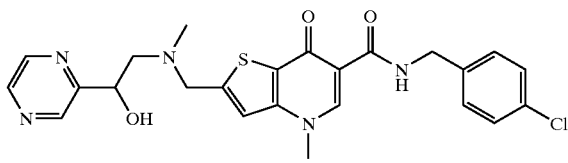

Racemic 2-(methylamino)-1-pyrazin-2-ylethanol (prepared from 2-acetylpyrazine by the procedure outlined in Preparations 10 and 11) was separated into individual enantiomers via chiral HPLC (5×50 cm Chiralpak AD column, 0.1% diethylamine/ethanol eluant, 70 mL/min flow rate, 310 mg sample loading). The slower eluting enantiomer (−optical rotation, 89% ee) was used to prepare the title compound (as described in Example 12). Recrystallization from acetonitrile/water afforded the title compound (38 mg) as a pale yellow solid.

Physical characteristics are as follows:

$^1$H NMR (400 MHz, DMSO-d$_6$) δ 10.45 (1 H), 8.74 (1H), 8.65 (1H), 8.54 (2H), 7.37 (5H), 5.65 (1H), 4.89 (1H), 4.54 (2H), 3.97 (3H), 3.89 (2H), 2.84 (2H), 2.13 (3H); MS (ES−) 496, 498; Anal. Found: C, 56.39; H, 4.81; N, 12.90.

EXAMPLE 17

N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide (enantiomer A)

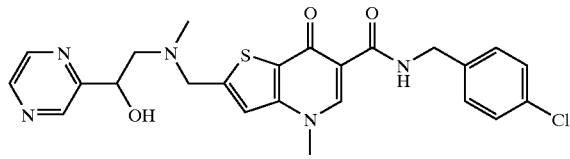

Racemic 2-(methylamino)-1-pyrazin-2-ylethanol (prepared from 2-acetylpyrazine by the procedure outlined in Preparations 10 and 11) was separated into individual enantiomers via chiral HPLC (5×50 cm Chiralpak AD column, 0.1% diethylamine/ethanol eluant, 70 mL/min flow rate, 310 mg sample loading). The faster eluting enantiomer (+optical rotation, 95% ee) was used to prepare the title compound (as described in Example 12). Recrystallization from acetonitrile/water afforded the title compound (38 mg) as a pale yellow solid.

Physical characteristics are as follows:

$^1$H NMR (400 MHz, DMSO-d$_6$) δ 10.45 (1 H), 8.74 (1H), 8.65 (1H), 8.54 (2H), 7.37 (5H), 5.65 (1H), 4.89 (1H), 4.54 (2H), 3.97 (3H), 3.89 (2H), 2.84 (2H), 2.13 (3H); MS (ES−) 496, 498; Anal. Found: C, 56.63; H, 4.84; N, 12.73.

EXAMPLE 18

2-{[(1-benzyl-2-hydroxyethyl)(methyl)amino]methyl}-N-(4-chlorobenzyl)-4-methyl-7-oxo-4,7-dihydrothieno[3,2-b]pyridine-6-carboxamide

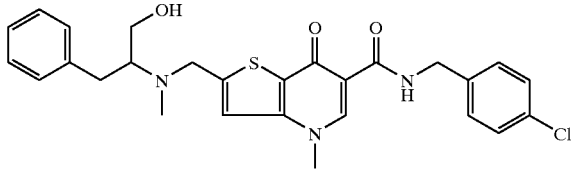

A mixture of N-(4-chlorobenzyl)-2-(chloromethyl)-4-methyl-7-oxo-4,7-dihydrothieno[3,2-b]pyridine-6-carboxamide (50 mg, 0.13 mmol), racemic 2-(methylamino)-3-phenylpropan-1-ol (Tetrahedron 2001, 57, 3425)(33 mg, 0.20 mmol) and diisopropylethylamine (35 μL, 0.20 mmol) in dry DMF (2.7 mL) was heated to 60° C., becoming a solution. The reaction was stirred for 10 hours at that temperature. After cooling to room temperature, the solution was diluted with water (7 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile (5 mL, dissolved with warming and then cooled to 0° C. overnight) gave the title compound (49 mg) as a white solid.

Physical characteristics are as follows:

$^1$H NMR (400 MHz, DMSO-d$_6$) δ 10.48 (1 H), 8.64 (1 H), 7.41, 7.17 (10 H), 4.53 (3 H), 4.01 (2 H), 3.95 (3 H), 3.59 (1 H), 3.46 (1 H), 2.98 (1 H), 2.72 (2 H), 2.32 (3 H); Anal. Found: C, 62.97; H, 5.52; N, 8.18, MS (ESI+) for C$_{27}$H$_{28}$ClN$_3$O$_3$S m/z 510, (M+H)$^+$; HRMS (FAB) calcd for C$_{27}$H$_{28}$ClN$_3$O$_3$S+H 510.1618, found 510.1611.

Preparation 16

N-[4-(2-bromoacetyl)phenyl]acetamide

To a suspension of 4-acetamidoacetophenone (Lancaster, 5.32 g, 0.03 mol) in 1,4-dioxane/diethyl ether (100 mL, 1:2, v/v) was added bromine (1.53 mL, 0.03 mol) via a syringe. The reaction mixture was stirred at room temperature for 4 hours until the color of the mixture was changed from brown to white. The solid was collected by filtration, washed with diethyl ether, and dried under high vacuum to give the title compound as a white solid (4.8 g).

Physical characteristics are as follows:

$^1$H NMR (400 MHz, DMSO-d$_6$) δ 10.36 (1 H), 7.96 (2 H), 7.73 (2 H), 4.85 (2 H), 2.10 (3 H); MS (ESI+) for C$_{10}$H$_{10}$BrNO$_2$ m/z 256 (M+H)$^+$, 258.

Preparation 17

N-[4-(2-bromo-1-hydroxyethyl)phenyl]acetamide

To a solution of N-[4-(2-bromoacetyl)phenyl]acetamide (2.1 g, 0.0082 mol, in 30 mL of methanol) was introduced solid NaBH$_4$ (1.0 g, 0.026 mol) at 0° C. and stirred at that temperature for 15 minutes. The mixture was diluted with diethyl ether (20 mL) and water (20 mL). The ether phase was separated and the aqueous phase was extracted with diethyl ether. The ether phases were combined and washed with brine, dried. Purification on a silica gel column gave the title compound as a white solid (0.40 g).

Physical characteristics are as follows:

$^1$H NMR (400 MHz, DMSO-d$_6$) δ 9.92 (1 H), 7.52 (2 H), 7.29 (2 H), 5.73 (1 H), 4.72 (1 H), 3.61 (1 H), 3.53 (1 H), 2.02 (3 H); MS (ESI+) for C$_{10}$H$_{12}$BrNO$_2$ m/z 258 (M+H)$^+$, 260.

Preparation 18

N-{4-[1-hydroxy-2-(methylamino)ethyl]phenyl}acetamide

To a solution of N-[4-(2-bromo-1-hydroxyethyl)phenyl]acetamide (0.40 g, in 10 mL of methanol) was introduced methylamine (10 mL, 2.0 M in methanol) at 0° C. The reaction mixture was warmed to room temperature after 30 minutes, and stirred at that temperature for 2 hours. The solvent and excess methylamine was evaporated. The residue was dissolved in methanol (5 mL) and stirred with resin (BioRad 50W×2, 0.5 g) overnight. The resin was collected by filtration, washed with methanol. The product on the resin was washed off with NH$_4$OH/CH$_3$OH (10% NH$_4$OH aqueous solution (Aldrich, 29.4% NH$_3$) in methanol, v/v). The solution was concentrated to give the title compound as a white solid (0.16 g).

Physical characteristics are as follows:

$^1$H NMR (400 MHz, DMSO-d$_6$) δ 9.89 (1 H), 7.50 (2 H), 7.23 (2 H), 5.15 (1 H), 4.56 (1 H), 2.59, 2.53 (2 H), 2.29 (3 H), 2.02 (3 H); MS (ESI+) for C$_{11}$H$_{16}$N$_2$O$_2$ m/z 209 (M+H)$^+$, 191.

EXAMPLE 19

2-{[{2-[4-(acetylamino)phenyl]-2-hydroxyethyl}(methyl)amino]methyl}-N-(4-chlorobenzyl)-4-methyl-7-oxo-4,7-dihydrothieno[3,2-b]pyridine-6-carboxamide

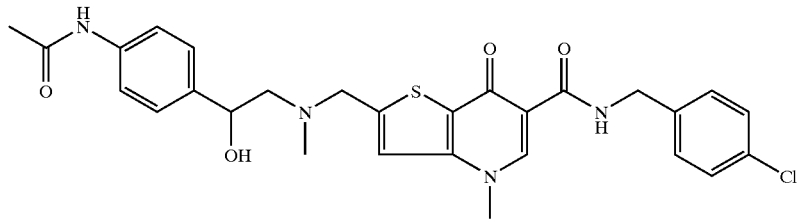

A mixture of N-(4-chlorobenzyl)-2-(chloromethyl)-4-methyl-7-oxo-4,7-dihydrothieno[3,2-b]pyridine-6-carboxamide (50 mg, 0.13 mmol), N-{4-[1-hydroxy-2-(methylamino)ethyl]phenyl}acetamide (42 mg, 0.20 mmol) and diisopropylethylamine (40 μL, 0.23 mmol) in dry DMF (2.7 mL) was heated to 60° C., becoming a solution. The reaction was stirred for 7 hours at that temperature. After cooling to room temperature, the solution was diluted with water (7 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with 3 mL of warming acetonitrile, cooled to room temperature, diluted with 2 mL of water, and then cooled to 0° C. overnight) gave the title compound (42 mg) as a white solid.

Physical characteristics are as follows:

$^1$H NMR (400 MHz, DMSO-d$_6$) δ 10.48 (1 H), 9.88 (1 H), 8.66 (1 H), 7.50 (2 H), 7.38 (5 H), 7.25 (2 H), 5.09 (1 H), 4.71 (1 H), 4.54 (2 H), 3.97 (3 H), 3.90 (2 H), 2.68, 2.53 (2 H), 2.30 (3 H), 2.02 (3 H); Anal. Found: C, 58.88; H, 5.33; N, 9.81. HRMS (FAB) calcd for C$_{28}$H$_{29}$ClN$_4$O$_4$S+H 553.1676, found 553.1675.

EXAMPLE 20

N-(4-chlorobenzyl)-2-{[[(2S)-2-hydroxy-2-pyridin-3-ylethyl](methyl)amino]methyl}-4-methyl-7-oxo-4,7-dihydrothieno[3,2-b]pyridine-6-carboxamide

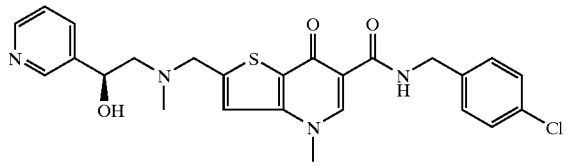

A mixture of N-(4-chlorobenzyl)-2-(chloromethyl)-4-methyl-7-oxo-4,7-dihydrothieno[3,2-b]pyridine-6-carboxamide (167 mg, 0.44 mmol), (1S)-2-(methylamino)-1-pyridin-3-ylethanol (Preparation 29) (100 mg, 0.66 mmol) and diisopropylethylamine (115 μL, 0.66 mmol) in dry DMF (8 mL) was heated to 60° C., becoming a solution. The reaction was stirred for 7 hours at that temperature. After cooling to room temperature, the solution was diluted with water (12 mL). The resulting milky suspension was stirred vigorously for 30 minutes, and then left standing overnight in the refrigerator. The mixture was filtered, and the collected solid was washed with water and dried in vacuo, leaving a white solid. Recrystallization from /water (dissolved with warming 5 mL of acetonitrile, then cooled to 0° C. and then diluted with 1 mL of water, left overnight) gave the title compound (125 mg) as a white solid.

Physical characteristics are as follows:

$^1$H NMR (400 MHz, DMSO-d$_6$) δ 10.47 (1 H), 8.66 (1 H), 8.55 (1 H), 8.45 (1 H), 7.74 (1 H), 7.38 (7 H), 5.39 (1 H), 4.83 (1 H), 4.54 (2 H), 4.00, 3.84 (6 H), 2.75, 2.62 (2 H), 2.31 (3 H); MS (CI) for C$_{25}$H$_{25}$ClN$_4$O$_3$S m/z 497 (M+H)$^+$, 499, 498, 497, 347, 153, 125, 108, 96, 69, 61; HRMS (FAB) calcd for C$_{25}$H$_{25}$ClN$_4$O$_3$S+H 497.1414, found 497.1436.

EXAMPLE 21

N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide

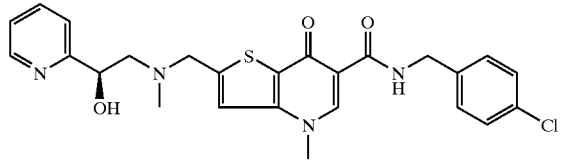

A mixture of N-(4-chlorobenzyl)-2-(chloromethyl)-4-methyl-7-oxo-4,7-dihydrothieno[3,2-b]pyridine-6-carboxamide (113 mg, 0.30 mmol), (1R)-2-(methylamino)-1-pyridin-2-ylethanol (Preparation 28) (100 mg, 0.44 mmol) and diisopropylethylamine (230 μL, 1.32 mmol) in dry DMF (8 mL) was heated to 60° C., becoming a solution. The reaction was stirred for 7 hours at that temperature. After cooling to room temperature, the solution was diluted with water (12 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with warming 5 mL of acetonitrile, then cooled to 0° C. and then diluted with 1 mL of water, left overnight) gave the title compound (98 mg) as a white solid.

Physical characteristics are as follows:

$^1$H NMR (400 MHz, DMSO-d$_6$) δ 10.48 (1 H), 8.66 (1 H), 8.48 (1 H), 7.78 (1 H), 7.50 (1 H), 7.41, 7.33 (6 H), 7.25 (1 H), 5.38 (1 H), 4.83 (1 H), 4.54 (2 H), 3.98 (4 H), 3.92 (2 H), 2.82 (1 H), 2.71 (1 H), 2.33 (3 H); Anal. Found: C, 59.78; H, 5.19; N, 10.38. MS (CI) for C$_{25}$H$_{25}$ClN$_4$O$_3$S m/z 497 (M+H)$^+$, 499, 497, 347, 153, 122, 108, 106, 96, 69, 61; HRMS (FAB) calcd for C$_{25}$H$_{25}$ClN$_4$O$_3$S+H 497.1414, found 497.1412.

EXAMPLE 22

N-(4-chlorobenzyl)-2-{[(2-hydroxy-2-pyrimidin-2-ylethyl)(methyl)amino]methyl}-4-methyl-7-oxo-4,7-dihydrothieno[3,2-b]pyridine-6-carboxamide

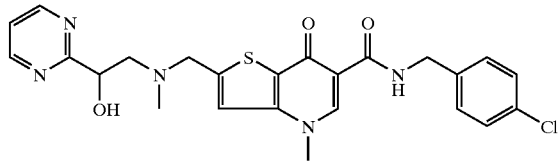

A mixture of N-(4-chlorobenzyl)-2-(chloromethyl)-4-methyl-7-oxo-4,7-dihydrothieno[3,2-b]pyridine-6-carboxamide (100 mg, 0.26 mmol), 2-(methylamino)-1-pyrimidin-2-ylethanol (Preparation 23)(59 mg, 0.39 mmol) and diisopropylethylamine (67 µL, 0.38 mmol) in dry DMF (5 mL) was heated to 60° C., becoming a solution. The reaction was stirred for 7 hours at that temperature. After cooling to room temperature, the solution was diluted with water (10 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with warming 5 mL of acetonitrile, then cooled to 0° C. and then diluted with 2 mL of water, left overnight) gave the title compound (60 mg) as a white solid.

Physical characteristics are as follows:

$^1$H NMR (400 MHz, DMSO-$d_6$) δ 10.47 (1 H), 8.78 (2 H), 8.65 (1 H), 7.43, 7.33 (6 H), 5.36 (1 H), 4.86 (1 H), 4.53 (2 H), 3.97 (3 H), 3.87 (2 H), 2.98 (1 H), 2.82 (1 H), 2.29 (3 H); MS (CI) for $C_{24}H_{24}ClN_5O_3S$ m/z 498 (M+H)$^+$, 500, 498, 349, 347, 154, 126, 109, 107, 96, 61; HRMS (FAB) calcd for $C_{24}H_{24}ClN_5O_3S$+H 498.1366, found 498.1385.

EXAMPLE 23

N-(4-chlorobenzyl)-2-{[[2-hydroxy-2-(1H-indol-3-yl)ethyl](methyl)amino]methyl}-4-methyl-7-oxo-4,7-dihydrothieno[3,2-b]pyridine-6-carboxamide

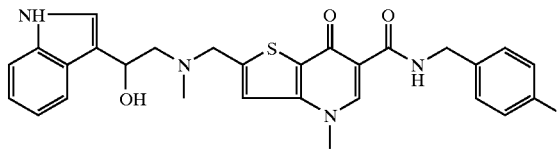

A mixture of N-(4-chlorobenzyl)-2-(chloromethyl)-4-methyl-7-oxo-4,7-dihydrothieno[3,2-b]pyridine-6-carboxamide (100 mg, 0.26 mmol), 1-(1H-indol-3-yl)-2-(methylamino)ethanol (Khim.-Farm. Zh. 1970, 4, 5–9)(75 mg, 0.39 mmol) and diisopropylethylamine (180 µL, 1.04 mmol) in dry DMF (5 mL) was heated to 60° C., becoming a solution. The reaction was stirred for 5 hours at that temperature. After cooling to room temperature, the solution was diluted with water (15 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with warming 5 mL of acetonitrile, then cooled to 0° C. and then diluted with 3 mL of water, left overnight) gave the title compound (59 mg) as a white solid.

Physical characteristics are as follows:

$^1$H NMR (400 MHz, DMSO-$d_6$) δ 10.87 (1 H), 10.48 (1 H), 8.66 (1 H), 7.54 (1 H), 7.41, 7.31 (6 H), 7.23 (1 H), 7.03 (1 H), 6.89 (1 H), 5.07 (1 H), 4.86 (1 H), 4.54 (2 H), 4.00, 3.89 (5 H), 2.83 (2 H), 2.38 (3 H); MS (CI) $C_{28}H_{27}ClN_4O_3S$ m/z 535 (M+H)$^+$, 535, 517, 347, 175, 173, 163, 146, 144, 118, 61; HRMS (FAB) calcd for $C_{28}H_{27}ClN_4O_3S$+H 535.1570, found 535.1581.

EXAMPLE 24

2-{[[2-(3-aminophenyl)-2-hydroxyethyl](methyl)amino]methyl}-N-(4-chlorobenzyl)-4-methyl-7-oxo-4,7-dihydrothieno[3,2-b]pyridine-6-carboxamide

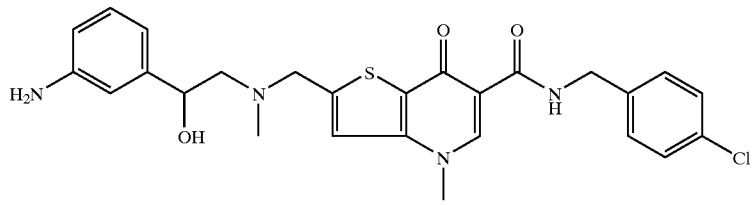

A mixture of N-(4-chlorobenzyl)-2-(chloromethyl)-4-methyl-7-oxo-4,7-dihydrothieno[3,2-b]pyridine-6-carboxamide (80 mg, 0.21 mmol), 1-(3-aminophenyl)-2-(methylamino)ethanol (Zhur. Obshchei Khim. (J. Gen. Chem.) 1952, 22, 496–502)(53 mg, 0.32 mmol) and diisopropylethylamine (67 µL, 0.38 mmol) in dry DMF (5 mL) was heated to 60° C., becoming a solution. The reaction was stirred for 5 hours at that temperature. After cooling to room temperature, the solution was diluted with water (15 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with warming 5 mL of acetonitrile, then cooled to 0° C. and then diluted with 3 mL of water, left overnight) gave the title compound (62 mg) as a white solid.

Physical characteristics are as follows:

$^1$H NMR (400 MHz, DMSO-$d_6$) δ 10.48 (1 H), 8.66 (1 H), 7.41, 7.33 (5 H), 6.92 (1 H), 6.56 (1 H), 6.46 (1 H), 6.41 (1 H), 4.96 (2 H), 4.61 (1 H), 4.54 (2 H), 3.98 (3 H), 3.91 (1 H), 2.59 (1 H), 2.33 (3 H); MS (CI ) for $C_{26}H_{27}ClN_4O_3S$ m/z 511 (M+H)$^+$, 513, 511, 347, 167, 165, 153, 149, 139, 136, 61; HRMS (FAB) calcd for $C_{26}H_{27}ClN_4O_3S$+H 511.1570, found 511.1562.

EXAMPLE 25

2-{[[2-(1,3-Benzodioxol-5-yl)-2-hydroxyethyl](methyl)amino]methyl}-N-(4-chlorobenzyl)-4-methyl-7-oxo-4,7-dihydrothieno[3,2-b]pyridine-6-carboxamide

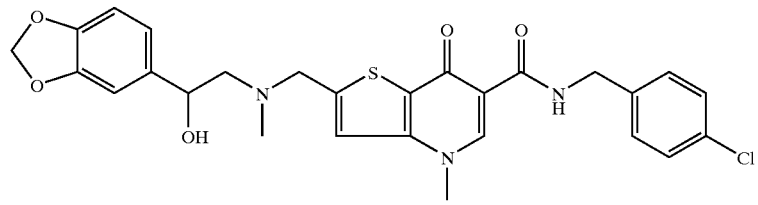

A mixture of N-(4-chlorobenzyl)-2-(chloromethyl)-4-methyl-7-oxo-4,7-dihydrothieno[3,2-b]pyridine-6-carboxamide (80 mg, 0.21 mmol), 1-(1,3-benzodioxol-5-yl)-2-(methylamino)ethanol (*Journal of Organometallic Chemistry*, 1998, 339, 267–75) (62 mg, 0.32 mmol) and diisopropylethylamine (67 µL, 0.38 mmol) in dry DMF (5 mL) was heated to 60° C., becoming a solution. The reaction was stirred for 5 hours at that temperature. After cooling to room temperature, the solution was diluted with water (15 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile/water (dissolved with warming 3 mL of acetonitrile, then cooled to 0° C. and then diluted with 2 mL of water, left overnight) gave the title compound (74 mg) as a white solid.

Physical characteristics are as follows:

$^1$H NMR (400 MHz, DMSO-d$_6$) δ 10.48 (1 H), 8.66 (1 H), 7.41, 7.33 (5 H), 6.88 (1 H), 6.82 (2 H), 5.97 (2 H), 5.11 (1 H), 4.68 (1 H), 4.54 (2 H), 3.98 (3 H), 3.89 (2 H), 2.68, 2.54 (2 H), 2.30 (3 H); Anal. Found: C, 59.82; H, 4.90; N, 7.71. MS (CI) for C$_{27}$H$_{26}$ClN$_3$O$_5$S m/z 540 (M+H)$^+$, 540, 347, 196, 194, 182, 180, 178, 168, 165, 61; HRMS (FAB) calcd for C$_{27}$H$_{26}$ClN$_3$O$_5$S+H 540.1360, found 540.1355.

EXAMPLE 26

N-(4-chlorobenzyl)-2-{[[2-hydroxy-2-(4-methoxyphenyl)ethyl](methyl)amino]methyl}-4-methyl-7-oxo-4,7-dihydrothieno[3,2-b]pyridine-6-carboxamide

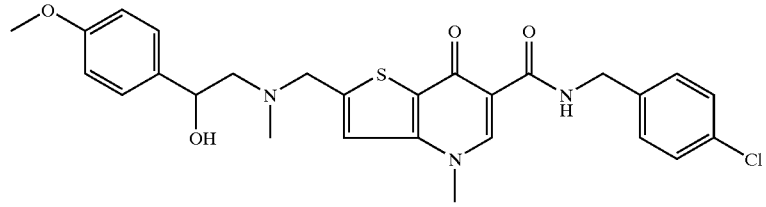

A mixture of N-(4-chlorobenzyl)-2-(chloromethyl)-4-methyl-7-oxo-4,7-dihydrothieno[3,2-b]pyridine-6-carboxamide (80 mg, 0.21 mmol), 1-(4-methoxyphenyl)-2-(methylamino)ethanol (*Tetrahedron* 1999, 55, 4831–4842) (58 mg, 0.32 mmol) and diisopropylethylamine (67 µL, 0.38 mmol) in dry DMF (5 mL) was heated to 60° C., becoming a solution. The reaction was stirred for 7 hours at that temperature. After cooling to room temperature, the solution was diluted with water (15 mL). The resulting milky suspension was stirred vigorously for 30 minutes, and then left standing overnight in the refrigerator. The mixture was filtered, and the collected solid was washed with water and dried in vacuo, leaving a white solid. Recrystallization from acetonitrile (5 mL, dissolved with warming and then cooled to 0° C. overnight) gave the title compound (54 mg) as a white solid.

Physical characteristics are as follows:

$^1$H NMR (400 MHz, DMSO-d$_6$) δ 10.48 (1 H), 8.67 (1 H), 7.38 (5 H), 7.25 (2 H), 6.87 (2 H), 5.06 (1 H), 4.72 (1 H), 4.54 (2 H), 3.98 (3 H), 3.90 (2 H), 3.73 (3 H), 2.67, 2.55 (2 H), 2.31 (3 H); Anal. Found: C, 61.41; H, 5.42; N, 7.86. MS (CI) for C$_{27}$H$_{28}$ClN$_3$O$_4$S m/z 526 (M+H)$^+$, 528, 526, 349, 347, 182, 164, 154, 151, 137, 61; HRMS (FAB) calcd for C$_{27}$H$_{28}$ClN$_3$O$_4$S+H 526.1567, found 526.1580.

Preparation 19

2-{1-[(Triisopropylsilyl)oxy]vinyl}pyrimidine

2-Acetylpyrimidine (Khim. Geterotsikl. Soedin., (7), 958–62; 1981)(7.37g, 60.4mmol) and DIEA (23.4 g, 181.2 mmol) were dissolved in dry CH$_2$Cl$_2$ under N$_2$ then cooled in an ice bath. TIPS-triflate (17.9 ml, 20.4 g, 66.4 mmol) was added over 2–3 min and stirred over night. The solvent was evaporated and the residue treated with ether (200 ml), filtered and washed with sat. sodium bicarbonate solution (2×50 ml). Evaporation gave a quantitative yield of the silyl ether as a red oil.

Physical characteristics are as follows:

HRMS (FAB) calcd for C$_{15}$H$_{26}$N$_2$OSi+H 279.1892, found 279.1898. $^1$H NMR (300 MHz, CDCl$_3$) δ 1.15 (18 H), 1.31 (3 H), 4.90 (1 H), 5.82 (1 H), 7.16 (1 H), 8.74 (2 H).

Preparation 20

2-{2-Chloro-1-[(triisopropylsilyl)oxy]ethenyl}pyrimidine. 737980

N-chlorosuccinimide (9.97 g, 74.7 mmol) was added to a solution of 2-{1-[(Triisopropylsilyl)oxy]vinyl}pyrimidine (17.3 g, 62.2 mmol) in dry THF (120 ml) under N$_2$ then heated at 65° for 5 hr. After cooling, ether (275 ml) was added and then washed with sat. sodium bicarbonate solution (2×100 ml). The organic layer was dried over sodium sulfate, filtered and evaporated to leave an amber oil. This oil was dissolved in hexane (250 ml), treated with MgSO$_4$ and filtered. Evaporation afforded the product as a yellow oil in quantitative yield.

Physical characteristics are as follows:
HRMS (FAB) calcd for $C_{15}H_{25}ClN_2OSi+H$ 313.1503, found 313.1509. $^1$H NMR (300 MHz, $CDCl_3$) δ 1.13 (18 H), 1.33 (3 H), 6.97 (1 H), 7.17 (1 H), 8.68 (2 H).

Preparation 21
2-Chloro-1-pyrimidin-2-ylethanone

2-{2-Chloro-1-[(triisopropylsilyl)oxy]ethenyl}pyrimidine (19.4 g, 62.2 mmol) was dissolved in acetonitrile (90 ml) and treated with 48% HF (10 ml) for 4 hr. Sat. sodium bicarbonate solution (ca. 250 ml) was then added carefully to pH7 and the mixture extracted with $CH_2Cl_2$ (3×200 ml). After drying ($Na_2SO_4$), filtration and evaporation two oils were obtained, the upper colorless oil was decanted off and discarded and the lower oil crystallized to an oily solid. Chromatography over silica gel (500 g) eluting with 2.5% MeOH—$CHCl_3$ gave the product as a pale yellow solid (6.50 g) mp:73–80°.

Physical characteristics are as follows:
Anal. Found: C, 46.05; H, 3.09; N, 17.93.

Preparation 22
rac-2-Chloro-1-pyrimidin-2-ylethanol

2-Chloro-1-pyrimidin-2-ylethanone (6.15 g, 39.3 mmol) was dissolved in ethanol (125 ml) and $CeCl_3.7H_2O$ (14.64 g, 39.3 mmol) was added. Stirring was continued for 10 min then sodium borohydride (1.49 g, 39.3 mmol) was added over 2 min. After 1 hr the solid was filtered and the filtrate evaporated. Sat. ammonium chloride solution (25 ml) was added followed by brine (250 ml) and the mixture adjusted to pH3-4 with 1N.HCl. Extraction with ethyl acetate (3×250 ml) afforded an amber oil which was chromatographed over silica gel (150 g) to give the product as a pale yellow oil (3.85 g)

Physical characteristics are as follows:
Anal. Found: C, 45.08; H, 4.47; N, 17.46.

Preparation 23
rac-2-(Methylamino)-1-pyrimidin-2-ylethanol

In a pressure bottle was placed 2-chloro-1-pyrimidin-2-ylethanol (3.525 g, 22.24 mmol), sodium iodide (0.344 g, 2.29 mmol) and a 2M. methylamine solution (160 ml, 320 mmol) in methanol. The bottle was sealed and heated at 62° for 17 hr. The solvent was evaporated and the residue stirred with 10% MeOH—$CHCl_3$. Filtration and evaporation gave a dark oil that was chromatographed over silica gel (90 g) eluting with 5–10% MeOH—$CH_2Cl_2$ containing 1% triethylamine The product was obtained as an amber oil (1.625 g).

Physical characteristics are as follows:
$^1$H NMR (400 MHz, $CDCl_3$) δ 2.53 (3 H), 3.03 (1 H), 3.21 (1 H), 3.66 (2 H), 5.03 (1 H), 7.26 (1 H), 8.77 (2H); HRMS (ESI) calcd for $C_7H_{11}N_3O+H$ 154.0980, found 154.0979.

Preparation 24
2-{1-[(triisopropylsilyl)oxy]vinyl}pyridine

2-Acetylpyridine (50 g, 0.413 mol) is placed in a 2 L 1N round bottom flask and anhydrous $CH_2Cl_2$ (Alrdich Sure Seal®, 0.65 L) is added, followed by the addition of i-$Pr_2$NEt (160.27 g, 1.24 mol, 3 eq., 216 mL). The flask is equipped with a 125 mL pressure equalized dropping funnel, and the mixture is placed under nitrogen and cooled in an ice-water bath. To the chilled ketone/amine mixture is added TIPSOTf (139.7 g, 0.456 mol, 1.1 eq., 122.6 mL) over 1.5 hours. The mixture is allowed to warm to room temperature overnight. The reaction mixture is concentrated in vacuo on a rotary evaporator (T≦25° C.) to give a yellow oil and a white solid. The flask contents are transferred to a 2 L separatory funnel with ether (1.2 L) resulting in the formation of additional white solid material (likely i$Pr_2$(Et)$NH^+$ -OTf which might be removed by filtration but is not in this experiment) and the mixture is washed with saturated aq. $NaHCO_3$ (2×0.65 L). The organic phase is separated, dried over $Na_2SO_4$, then is concentrated in vacuo to furnish the crude 2-[1-Tri-isopropylsilyloxy-vinyl]-pyridine (131.5 g) as a yellow-orange oil. This crude material is not further purified, but is immediately carried to the next step.

Physical characteristics are as follows:
$^1$H—NMR (400 MHz, $CDCl_3$): δ=8.57, 7.71, 7.21, 5.65, 4.58, 1.36, 1.15.

Preparation 25
2-{2-chloro-1-[(triisopropylsilyl)oxy]ethenyl}pyridine

Crude 2-{1-[(triisopropylsilyl)oxy]vinyl}pyridine (131.5 g, assumed 0.413 mmol) is placed in a 2 L, 1N round bottom flask and dissolved in anhydrous THF (Aldrich Sure Seal, 0.6 L). The flask is equipped with a reflux condenser and the apparatus is placed under nitrogen. NCS (60.66 g, 0.454 mol, 1.1 eq.) is added and the mixture is heated to reflux and maintained at reflux for 2 hours. The reaction mixture is cooled to room temperature, poured into a 4 L separatory funnel containing ether (1.5 L), and is washed with saturated aq. $NaHCO_3$ (2×0.7 L). The organic phase is separated, dried ($Na_2SO_4$), and concentrated in vacuo affords the target (117.5 g) as a yellow-orange oil. The crude material is not further purified, but is immediately carried into the next step.

Physical characteristics are as follows:
$^1$H-NMR (400 MHz, $CDCl_3$):δ=8.53, 7.71, 7.52, 7.22, 6.58, 1.21, 1.13.

Preparation 26
2-chloro-1-pyridin-2-ylethanone

Crude 2-{2-chloro-1-[(triisopropylsilyl)oxy]ethenyl}pyridine (117.3 g, 0.376 mol) is placed in a 4 L plastic bottle and is dissolved in acetonitrile (0.4 L). To the stirring solution is added 48% aqueous HF (170 mL, 0.45 mL/mmol) and the progress of the reaction is monitored by reverse phase analytical HPLC. After. Ca. 2 hours the reaction is judged to be complete, and the pH of the solution is carefully adjusted to ca. 8 with saturated aq. $NaHCO_3$. The mixture is poured into a separatory funnel containing $CH_2Cl_2$ (1.5 L). The organic phase is removed and the aq. layer is extracted with $CH_2Cl_2$ (2×1.0 L). The combined organic layers are dried ($Na_2SO_4$), and concentration in vacuo affords the title compound (49.5 g) as a tan solid (after cooling). The crude material is judged to be quite pure by $^1$H—NMR and HPLC and is used as is in the Noyori asymmetric reduction.

Physical characteristics are as follows:
$^1$H—NMR (400 MHz, $CDCl_3$): δ=8.66, 8.09, 7.88, 7.54, 5.12.

Preparation 27
(1S)-2-chloro-1-pyridin-2-ylethanol

[$RuCl_2(\eta^6$-p-cymene)]$_2$ (0.84 g, 1.37 mmol), $Et_3N$ (0.67 g, 6.66 mmol, 0.93 mL), and (1R, 2R)-N-p-toluenesulfonyl-1,2-diphenylethylenediamine (1.0 g, 2.72 mmol, 1.78 mol % based upon ketone) are combined in a 500 mL 1N round bottom flask. i-PrOH is added, a reflux condenser is attached and the mixture is warmed under reflux, and maintained, for 1 hour. Cool to room temperature and concentrate in vacuo (rotovapor followed by vacuum pump) to furnish the catalyst as a brown powdery solid. To the catalyst is added anhydrous DMF (Aldrich Sure Seal, 225 mL), followed in order by 2-chloro-1-pyridin-2-ylethanone (23.88 g, 0.153 mol) and HCOOH/$Et_3N$ (5:2, Fluka, 55 mL). After ca. 2–3 minutes of stirring (room temperature) bubbles (presumed to be $CO_2$) are apparent, emanating from the stirring vortex of the red-black solution. Reaction progress is monitored by reverse phase analytical HPLC, and after 65 minutes of stirring, the starting material is consumed (95:5 NaH$_2$PO$_4$/ H$_3$PO$_4$ buffered water/CH$_3$CN to 5:95, 17 minutes; retention time of starting chloroketone: 7.39 minutes, retention time of halohydrin 2.66 minutes). Quench the reaction by adding MeOH (25 mL), stir 5 minutes and then the DMF, etc is removed in vacuo (cold finger rotovapor, vacuum pump) to give a red-black viscous oil. The crude material is taken up in Et$_2$O/CH$_2$Cl$_2$ (4:1, 1.25 L), placed in a 3 L separatory funnel, washed with saturated aq. NaHCO$_3$ (1.0 L), brine (1.0 L), and dried (Na$_2$SO$_4$). Filtration and concentration in vacuo affords the crude product as a red-orange oil which is purified by chromatography on a column of silica gel (70 mm OD, 250 g 230–400 mesh, packed hexanes; compound applied in CH$_2$Cl$_2$/hexanes 60:40; eluted with hexanes/Et$_2$O (75:25 2 L; 65:35 2 L; 55:45 2 L; 350 mL fractions) using the flash technique. Fractions 11–17 are combined to afford 16.41 g of the target as a pale yellow solid.

Physical characteristics are as follows:
MP: 49–50° C.; $^1$H—NMR (400 MHz, CDCl$_3$): δ=8.60, 7.77, 7.58, 7.30, 5.00, 4.20, 3.85; EI-MS (70EV): 160(M$^+$, 35), 158(M$^+$, 90), 122(90), 106(base); Anal. Found: C, 53.27; H, 5.19; N, 8.81, Cl, 22.29. Specific Rotation $[\alpha]^P_{25}$= 62 (c 0.94, methanol).

Preparation 28

(1R)-2-(methylamino)-1-pyridin-2-ylethanol (1S)-2-chloro-1-pyridin-2-ylethanol (6.0 g, 38 mmol) and NaI (0.57 g, 3.8 mmol) are combined in a 500 mL, plastic coated, thick walled bottle and are covered with 2M MeNH$_2$ in MeOH (0.19 L). The Teflon stopper is wrapped in Teflon tape, the bottle is sealed. Stirring is started, and the bottle is immersed in a 60° C. oil bath for 16 hours. The yellow-brown mixture is cooled to room temperature and analyzed by analytical reverse phase HPLC, which indicated that the reaction is complete (retention time starting material=2.44 minutes; retention time product=1.24 minutes). Concentration in vacuo affords the crude product as a yellow oil, which is treated with CH$_2$Cl$_2$-THF (0.25 L, 10:90) to give a yellow solution and a white precipitate. The precipitate is removed by filtration, is rinsed with CH$_2$Cl$_2$-THF (10:90) and the combined filtrated are concentrated in vacuo to give a yellow-brown oil. The crude product is purified by chromatography on a column of silica gel (70 mm OD, 250 g, 230–400 mesh; packed with CH$_2$Cl$_2$-MeOH 90:10; eluted with CH$_2$Cl$_2$-MeOH 90:10, 2 L, 500 mL fractions; CH$_2$Cl$_2$-MeOH—NH$_4$OH 89:10:1, 8 L, 350 mL fractions) using the flash technique. Fractions 14–30 are combined to provide 3.18 g of the target as an amber oil.

Physical characteristics are as follows:
$^1$H—NMR (400 MHz, DMSO-d$_6$): δ=8.49, 7.79, 7.52, 7.25, 4.75, 2.90, 2.67, 2.32; EI-MS (70EV): 153(M$^+$, base), 135(18), 122(20), 108(62); HRMS (FAB): Found 153.1009; Specific Rotation $[\alpha]^P_{25}$=49 (c 0.36, CH$_2$Cl$_2$).

Preparation 29

(1S)-2-(methylamino)-1-pyridin-3-ylethanol

As described for the preparation of (1R)-2-(methylamino)-1-pyridin-2-ylethanol (Preparations 27–28), 3-chloroacetylpyridine (*Chem. Ber.* 1951, 84, 147–149) is converted to the title compound, isolated as a pale yellow amorphous solid.

Physical characteristics are as follows:
OAMS supporting ions at: ESI+153.1 ESI–151.1; HRMS (ESI) Found 153.1017; Specific Rotation $[\alpha]^{25}_D$=70° (c 1.03, methylene chloride); Anal. Found: C, 62.39; H, 7.93; N, 18.00.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

wherein:
G is phenyl substituted with from one to five R$^1$ substituents;
each R$^1$ is independently
(a) Cl,
(b) Br,
(c) F,
(d) cyano,
(e) C$_{1-7}$alkyl, or
(d) NO$_2$;
R$^2$ is
(a) H,
(b) R$^5$,
(c) NR$^7$R$^8$,
(d) SO$_2$R$^9$, or
(e) OR$^6$;
R$^3$ is
(a) H,
(b) halo,
(c) aryl,
(d) S(O)$_m$R$^6$,
(e) (C=O)R$^6$,
(f) (C=O)OH,
(g) (C=O)OR$^9$,
(h) cyano,
(i) het, wherein the het is bound via a carbon atom or a nitrogen atom,
(j) OR$^{14}$,
(k) NR$^7$R$^8$,
(l) SR$^{14}$,
(m) NHSO$_2$R$^{12}$,
(n) C$_{1-7}$alkyl which is optionally partially unsaturated and optionally substituted by one or more R$^{11}$ substituents, or
(o) C$_{3-8}$cycloalkyl which is optionally partially unsaturated and optionally substituted by one or more R$^{11}$, or substituted by one or mere C$_{1-7}$alkyl which C$_{1-7}$alkyl is optionally substituted by one or more R$^{11}$;
R$^5$ is
(a) (CH$_2$CH$_2$O)$_i$R$^{10}$,
(b) het, wherein the het is bound via a carbon atom,
(c) aryl,
(d) C$_{1-7}$alkyl which is optionally partially unsaturated and optionally substituted by one or more R$^{11}$ substituents, or
(e) C$_{3-8}$cycloalkyl which is optionally partially unsaturated and optionally substituted by one or more R$^{11}$, or substituted by one or more C$_{1-7}$alkyl which C$_{1-7}$alkyl is optionally substituted by one or more R$^{11}$;

$R^6$ is
- (a) $C_{1-7}$alkyl optionally substituted by aryl, het, $OR^{13}$, $SR^{13}$, $NR^{13}R^{13}$, halo, or $C_{3-8}$cycloalkyl, which $C_{3-8}$cycloalkyl is optionally substituted with $OR^{13}$,
- (b) $C_{3-8}$cycloalkyl which is optionally partially unsaturated and optionally substituted by one or more halo, $OR^{13}$, $SR^{13}$, or $NR^{13}R^{13}$ substituents,
- (c) $NR^7R^8$,
- (d) aryl, or
- (e) het, wherein the het is bound via a carbon atom;

$R^7$ and $R^8$ are independently
- a. H,
- b. aryl,
- c. $C_{1-7}$alkyl which is optionally partially unsaturated and optionally substituted by one or more $NR^{13}R^{13}$, $OR^{14}$, $SR^{14}$, $S(O)_mR^9$, $P(=O)(OR^{14})(R^{14})$, $CONR^{14}R^{14}$, $CO_2R^{13}$, $(C=O)R^9$, het, aryl cyano, or halo substituents,
- d. $C_{3-8}$cycloalkyl which is optionally partially unsaturated an optionally substituted by one or more halo, $OR^{13}$, $SR^{13}$, oxo, or $NR^{13}R^{13}$ substituents,
- e. $(C=O)R^9$, or
- f. $R^7$ and $R^8$ together with the nitrogen to which they are attached form a het;

$R^9$ is
- (a) aryl,
- (b) het,
- (c) $C_{3-8}$cycloalkyl, or
- (d) $C_{1-7}$alkyl which is optionally partially unsaturated and optionally substituted by one or more $NR^{13}R^{13}$, $OR^{14}$, $SR^{14}$, halo, $CONR^{13}R^{13}$, $CO_2R^{13}$, het, or aryl substituents;

$R^{10}$ is
- (a) H, or
- (b) $C_{1-7}$alkyl optionally substituted by OH;

$R^{11}$ is
- (a) $OR^{14}$,
- (b) $SR^{14}$,
- (c) $NR^7R^8$,
- (d) halo,
- (e) $CONH_2$,
- (f) $CONHR^9$,
- (g) $CONR^9R^9$,
- (h) $CO_2H$,
- (i) $CO_2R^9$,
- (j) het,
- (k) aryl,
- (l) cyano,
- (m) oxo,
- (n) $SO_mR^6$, or
- (o) $P(=O)(OR^{14})(R^{14})$;

$R^{12}$ is
- (a) H,
- (b) het,
- (c) aryl,
- (d) $C_{3-8}$cycloalkyl optionally substituted with $R^{11}$, or
- (e) $C_{1-7}$alkyl optionally substituted with $R^{11}$;

$R^{13}$ is
- (a) H, or
- (b) $C_{1-7}$alkyl;

$R^{14}$ is
- (a) H,
- (b) aryl,
- (c) het,
- (d) $C_{1-7}$alkyl which is optionally partially unsaturated and optionally substituted by aryl, het, $OR^{13}$, $SR^{13}$, $NR^{13}R^{13}$, halo, or $C_{3-8}$cycloalkyl which $C_{3-8}$cycloalkyl is optionally substituted by one or more $OR^{13}$, or
- (e) $C_{3-8}$cycloalkyl which is optionally partially unsaturated and optionally substituted by one or more halo, $OR^{13}$, $SR^{13}$, or $NR^{13}R^{13}$ substituents;

$R^{15}$ is
- (a) H,
- (b) halo,
- (c) $OR^{13}$,
- (d) $SR^{13}$,
- (e) $NR^{13}R^{13}$,
- (f) $O(CH_2CH_2O)_nR^{10}$,
- (g) phenyl,
- (h) cyano,
- (i) nitro,
- (j) $CONR^{13}R^{13}$,
- (k) $CO_2R^{13}$,
- (l) $S(O)_mNR^{13}R^{13}$,
- (m) $CONHR^{13}$,
- (n) $S(O)_mR^{10}$,
- (o) $NR^{13}COR^{13}$,
- (p) $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, or
- (q) $C_{3-8}$cycloalkyl which is optionally partially unsaturated and optionally substituted by one or more oxo, halo, $OR^{13}$, $SR^{13}$, $C_{1-7}$alkyl , $CONH_2$ or $NR^{13}R^{13}$ substituents; or
- (r) pyrimidinyl, pyridyl, pyrrolyl, pyrazinyl, pyridazinyl, imidazolyl, or pyrazolyl;

each i is independently 2, 3, or 4;

each n is independently 1, 2, 3, 4 or 5;

each m is independently 1 or 2;

wherein any aryl other than G is optionally substituted with one or more $R^{15}$ substituents; and wherein any het is independently a 4–16 member saturated or unsaturated monocyclic, bicyclic, or tricyclic ring system having 1, 2, 3, or 4 heteroatoms selected from oxygen, sulfur, sulfinyl, sulfonyl, nitrogen, and an N-oxide and is optionally substituted with one or more =O, =N—$OR^{13}$, or $R^{15}$ substituents; or a pharmaceutically acceptable salt thereof.

2. The compound of claim 1 wherein $R^1$ is F, Cl, or cyano.

3. The compound of claim 2 wherein $R^1$ is Cl.

4. The compound of claim 3 wherein $R^1$ is 4-Cl.

5. The compound of claim 1 wherein $R^1$ is $C_{1-7}$alkyl.

6. The compound of claim 5 wherein $R^1$ is methyl.

7. The compound of claim 1 wherein $R^2$ is H.

8. The compound of claim 1 wherein $R^2$ is $C_{1-7}$alkyl which is optionally partially unsaturated and is optionally substituted with one or more $R^{11}$ substituents.

9. The compound of claim 8 wherein $R^2$ is methyl.

10. The compound of claim 8 wherein $R^2$ is ethyl.

11. The compound of claim 1 wherein $R^3$ is H, halo, aryl, $S(O)_mR^6$, $(C=O)R^6$, $(C=O)OH$, $(C=O)R^9$, cyano, $OR^{14}$, $NR^7R^8SR^{14}$, or $NHSO_2R^{12}$.

12. The compound of claim 1 wherein $R^3$ is $C_{1-7}$alkyl which is optionally partially unsaturated and optionally substituted by one or more $R^{11}$ substituents, or $C_{3-8}$cycloalkyl which is optionally partially unsaturated and optionally substituted by one or more $R^{11}$ or $C_{1-7}$alkyl substituents.

13. The compound of claim 12 wherein $R^3$ is hydroxymethyl.

14. The compound of claim 12 wherein $R^3$ is $C_{2-7}$alkyl which comprises one double bond and is optionally substituted by one or more $R^{11}$ substituents.

15. The compound of claim 12 wherein $R^3$ is $C_{2-7}$alkyl which comprises one triple bond and is optionally substituted by one or more $R^{11}$ substituents.

16. The compound of claim 15 wherein $R^3$ is 3-hydroxypropyn-1-yl.

17. The compound of claim 1 wherein $R^3$ is het, wherein the het is bound to the thieno ring via a carbon atom.

18. The compound of claim 1 wherein $R^3$ is het, wherein the het is bound to the thieno ring via a nitrogen atom.

19. The compound of claim 1 wherein $R^3$ is H.

20. The compound of claim 1 wherein $R^3$ is $CH_2NR^7R^8$.

21. The compound of claim 1 wherein $R^3$ is $CH_2NR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_mR^9$, $CONR^{13}R^{13}$, $CO_2R^{13}$, $(C=O)R^9$, het, aryl, cyano, or halo substituents.

22. The compound of claim 1 wherein $R^3$ is $CH_2NR^7R^8$ where $R^7$ is methyl, and $R^8$ is ethyl substituted with aryl, het, or $OR^{14}$.

23. The compound of claim 1 wherein $R^3$ is morpholinomethyl.

24. The compound of claim 1 wherein $R^3$ is N-methyl-N-{2-(4-hydroxyphenyl)-2-hydroxyethyl}aminomethyl; N-methyl-N-{2-(3-hydroxyphenyl)-2-hydroxyethyl}aminomethyl; N-methyl-N-{2-(3-methoxyphenyl)-2-hydroxyethyl}aminomethyl; N-methyl-N-(2-furan-2-yl-2-hydroxyethyl)aminomethyl; N-methyl-N-{2-phenyl-2-hydroxyethyl}aminomethyl; N-methyl-N-{2-(1,3-thiazol-2-yl)ethyl}aminomethyl; N-methyl-N-{2-(4-methylsulfonylphenyl)-2-hydroxyethyl}aminomethyl; N-methyl-N-{2-(pyridin-2-yl)-2-hydroxyethyl}aminomethyl; N-methyl-N-(2-pyrazin-2-yl-2-hydroxyethyl)aminomethyl; N-methyl-N-[2-(5-cyanothien-2-yl)-2-hydroxyethyl]aminomethyl; N-methyl-N-(2-pyridin-2-yl-2-hydroxyethyl)aminomethyl; N-methyl-N-(2-pyrimidin-2-yl-2-hydroxyethyl)aminomethyl; N-methyl-N-[2-(4-acetylaminophenyl)-2-hydroxyethyl]aminomethyl; (R)-N-methyl-N-(2-pyridin-3-yl-2-hydroxyethyl)aminomethyl; or 3-hydroxy-1-propynyl; hydroxymethyl; morpholinomethyl; (R)-N-methyl-N-{2-(pyridin-2-yl)-2-hydroxyethyl}aminomethyl; N-methyl-N-{2-indol-3-yl-2-hydroxyethyl}aminomethyl; N-methyl-N-{2-(3-aminophenyl)-2-hydroxyethyl}aminomethyl; N-methyl-N-{2-(3,4-methylenedioxyphenyl)-2-hydroxyethyl}aminomethyl; or N-methyl-N-{2-(4-methoxyphenyl)-2-hydroxyethyl}aminomethyl.

25. The compound of claim 1 which is a compound of formula IV:

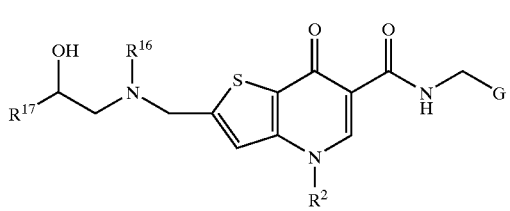

IV wherein:
$R^{16}$ is
(a) H,
(b) aryl,
(c) $C_{1-7}$alkyl which is optionally partially unsaturated and is optionally substituted by one or more $NR^{13}R^{13}$, $OR^{14}$, or $SR^{14}$, $S(O)_mR^9$, $CONR^{14}R^{14}$, $CO_2R^{13}$, $(C=O)R^9$, het, aryl, cyano, or halo substituents,
(d) $C_{3-8}$cycloalkyl which is optionally partially unsaturated and is optionally substituted by one or more halo, $OR^{13}$, $SR^{13}$, oxo, or $NR^{13}R^{13}$ substituents, or
(e) $(C=O)R^9$; and
$R^{17}$ is
(a) aryl, or
(b) het;
or a pharmaceutically acceptable salt thereof.

26. The compound of claim 25 which is a compound of formula V:

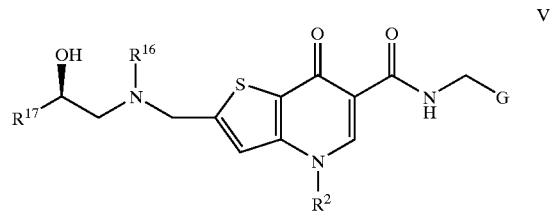

V or a pharmaceutically acceptable salt thereof.

27. The compound of claim 25 which is a compound of formula VI:

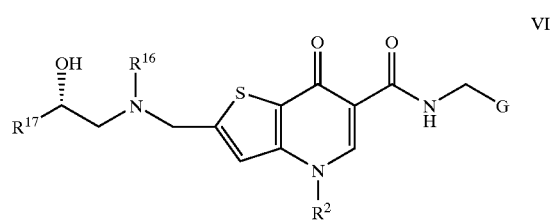

VI or a pharmaceutically acceptable salt thereof.

28. The compound of claim 1, 25, 26, or 27 wherein G is phenyl substituted with one, two, or three $R^1$ groups.

29. The compound of claim 1, 25, 26, or 27 wherein G is 4-chlorophenyl, 4-fluorophenyl, 3,4-dichlorophenyl, 3,4-difluorophenyl, 2,4-dichlorophenyl, 2,4-difluorophenyl, 4-chloro-2-fluorophenyl, 2-chloro-4-fluorophenyl, 3,4,5-trifluorophenyl, 4-bromophenyl, 4-methylphenyl, 4-cyanophenyl, or 4-nitrophenyl.

30. The compound of claim 1, 25, 26, or 27 wherein G is phenyl substituted with one or two $R^1$, and $R^2$ and $R^3$ are $C_{1-7}$alkyl which are optionally partially unsaturated and optionally substituted with one or more $R^{11}$ substituents.

31. The compound of claim 1, 25, 26, or 27 wherein G is phenyl substituted with one $R^1$ at the 4-position; $R^2$ is $CH_3$; and $R^3$ is $C_{1-7}$alkyl optionally substituted by $NR^7R^8$.

32. The compound of claim 1, 25, 26, or 27 wherein G is 4-chlorophenyl; $R^3$ is $CH_2N(CH_3)CH_2CH(OH)$aryl or $CH_2N(CH_3)CH_2CH(OH)$het; and $R^2$ is $CH_3$.

33. The compound of claim 1 wherein $R^{15}$ is NH—C(=O)—$R^{13}$.

34. The compound of claim 1, which is:

a) N-(4-Chlorobenzyl)-7-hydroxythieno[3,2-b]pyridine-6-carboxamide;
b) N-(4-Chlorobenzyl)-4-ethyl-7-oxo-4,7-dihydrothieno[3,2-b]pyridine-6-carboxamide;
c) N-(4-chlorobenzyl)-2-(3-hydroxyprop-1-ynyl)-4-methyl-7-oxo-4,7-dihydrothieno[3,2-b]pyridine-6-carboxamide;

d) N-(4-chlorobenzyl)-4-methyl-2-(morpholin-4-ylmethyl)-7-oxo-4,7-dihydrothieno[3,2-b]pyridine-6-carboxamide;
e) N-(4-chlorobenzyl)-2-{[[2-hydroxy-2-(3-methoxyphenyl)ethyl](methyl)amino]methyl}-4-methyl-7-oxo-4,7-dihydrothieno[3,2-b]pyridine-6-carboxamide;
f) N-(4-chlorobenzyl)-2-{[[2-(2-furyl)-2-hydroxyethyl](methyl)amino]methyl}-4-methyl-7-oxo-4,7-dihydrothieno[3,2-b]pyridine-6-carboxamide;
g) N-(4-chlorobenzyl)-2-{[(2-hydroxy-2-phenylethyl)(methyl)amino]methyl}-4-methyl-7-oxo-4,7-dihydrothieno[3,2-b]pyridin -6-carboxamide;
h) N-(4-chlorobenzyl)-2-{[[2-hydroxy-2-(1,3-thiazol-2-yl)ethyl](methyl)amino]methyl}-4-methyl-7-oxo-4,7-dihydrothieno[3,2-b]pyridine-6-carboxamide;
i) N-(4-chlorobenzyl)-2-{[{2-hydroxy-2-[4-(methylsulfonyl)phenyl]ethyl}(methyl)amino]methyl}-4-methyl-7-oxo-4,7-dihydrothieno[3,2-b]pyridine-6-carboxamide;
j) N-(4-chlorobenzyl)-2-{[(2-hydroxy-2-pyridin-2-ylethyl)(methyl)amino]methyl}-4-methyl-7-oxo-4,7-dihydrothieno[3,2-b]pyridine-6-carboxamide;
k) N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide;
l) N-(4-chlorobenzyl)-2-{[[2-(5-cyanothien-2-yl)-2-hydroxyethyl](methyl)amino]methyl}-4-methyl-7-oxo-4,7-dihydrothieno[3,2-b]pyridine-6-carboxamide;
m) N-(4-chlorobenzyl)-2-{[[2-hydroxy-2-(4-hydroxyphenyl)ethyl](methyl)amino]methyl}-4-methyl-7-oxo-4,7-dihydrothieno[3,2-b]pyridine-6-carboxamide;
n) N-(4-chlorobenzyl)-2-{[[2-(2-furyl)-2-hydroxyethyl](methyl)amino]methyl}-4-{2-[methoxy(methyl)amino]-2-oxoethyl}-7-oxo-4,7-dihydrothieno[3,2-b]pyridine-6-carboxamide;
o) N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide;
p) 2-{[(1-benzyl-2-hydroxyethyl)(methyl)amino]methyl}-N-(4chlorobenzyl)-4-methyl-7-oxo-4,7-dihydrothieno[3,2-b]pyridin -6-carboxamide;
q) 2-{[{2-[4-(acetylamino)phenyl]-2-hydroxyethyl}(methyl)amino]-methyl}-N-(4-chlorobenzyl)-4-methyl-7-oxo-4,7-dihydrothieno[3,2-b]pyridine-6-carboxamide;
r) N-(4-chlorobenzyl)-2-{[[(2S)-2-hydroxy-2-pyridin-3-ylethyl](methyl)amino]methyl}-4-methyl-7-oxo-4,7-dihydrothieno[3,2-b]pyridine-6-carboxamide;
s) N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide;
t) N-(4-chlorobenzyl)-2-{[(2-hydroxy-2-pyrimidin-2-ylethyl)(methyl)amino]methyl}-4-methyl-7-oxo-4,7-dihydrothieno[3,2-b]pyridine-6-carboxamide;
u) -(4-chlorobenzyl)-2-{[[2-hydroxy-2-(1H-indol-3-yl)ethyl](methyl)amino]methyl}-4-methyl-7-oxo-4,7-dihydrothieno[3,2-b]pyridine-6-carboxamide;
v) 2-{[[2-(3-aminophenyl)-2-hydroxyethyl](methyl)amino]methyl}-N-(4-chlorobenzyl)-4-methyl-7-oxo-4,7-dihydrothieno[3,2-b]pyridine-6-carboxamide;
w) 2-{[[2-(1,3-Benzodioxol-5-yl)-2-hydroxyethyl](methyl)amino]methyl}-N-(4-chlorobenzyl)-4-methyl-7-oxo-4,7-dihydrothieno[3,2-b]pyridine-6-carboxamide; or
x) N-(4-chlorobenzyl)-2-{[[2-hydroxy-2-(4-methoxyphenyl)ethyl]-(methyl)amino]methyl}-4-methyl-7-oxo-4,7-dihydrothieno[3,2-b]pyridine-6-carboxamide; or a pharmaceutically acceptable salt thereof.

35. The compound of claim 1, which is:

a) N-(4-chlorobenzyl)-2-{[[2-hydroxy-2-(3-methoxyphenyl)ethyl](methyl)amino]methyl}-4-methyl-7-oxo-4,7-dihydrothieno[3,2-b]pyridine-6-carboxamide;
b) N-(4-chlorobenzyl)-2-{[[2-(2-furyl)-2-hydroxyethyl](methyl)amino]methyl}-4-methyl-7-oxo-4,7-dihydrothieno[3,2-b]pyridine-6-carboxamide;
c) N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide;
d) N-(4-chlorobenzyl)-2-{[2-hydroxy-2-pyrimidin-2-ylethyl)(methyl)amino]methyl}-4-methyl-7-oxo-4,7-dihydrothieno[3,2-b]pyridine-6-carboxamide;
e) N-(4-chlorobenzyl)-2-{[[2-hydroxy-2-(1H-indol-3-yl)ethyl](methyl)amino]methyl}-4-methyl-7-oxo-4,7-dihydrothieno[3,2-b]pyridine-6-carboxamide;
f) 2-{[[2-(3-aminophenyl)-2-hydroxyethyl](methyl)amino]methyl}-N-(4-chlorobenzyl)-4-methyl-7-oxo-4,7-dihydrothieno[3,2-b]pyridine-6-carboxamide;
g) N-(4-chlorobenzyl)-2-{[2-hydroxy-2-pyridin-2-ylethyl)(methyl)amino]methyl}-4-methyl-7-oxo-4,7-dihydrothieno[3,2-b]pyridine-6-carboxamide;
h) N-(4-chlorobenzyl)-2-{[[2-(5-cyanothien-2-yl)-2-hydroxyethyl](methyl)amino]methyl}-4-methyl-7-oxo-4,7-dihydrothieno[3,2-b]pyridine-6-carboxamide;
i) N-(4-chlorobenzyl)-2-{[[2-hydroxy-2-(4-hydroxyphenyl)ethyl](methyl)amino]methyl}-4-methyl-7-oxo-4,7-dihydrothieno[3,2-b]pyridine-6-carboxamide;
j) 2-{[(1-benzyl-2-hydroxyethyl)(methyl)amino]methyl}-N-(4-chlorobenzyl)-4-methyl-7-oxo-4,7-dihydrothieno[3,2-b]pyridin-6-carboxamide;
k) N-(4-chlorobenzyl)-2-{[[(2S)-2-hydroxy-2-pyridin-3-ylethyl](methyl)amino]methyl}-4-methyl-7-oxo-4,7-dihydrothieno[3,2-b]pyridine-6-carboxamide;
l) N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide; or
m) 2-{[[2-(1,3-Benzodioxol-5-yl)-2-hydroxyethyl](methyl)amino]-methyl}-N-(4-chlorobenzyl)-4-methyl-7-oxo-4,7-dihydrothieno[3,2-b]pyridine-6-carboxamide;

or a pharmaceutically acceptable salt thereof.

36. The compound of claim 1, which is:

a) N-(4-chlorobenzyl)-2-{[[2-hydroxy-2-(3-methoxyphenyl)ethyl](methyl)amino]methyl}-4-methyl-7-oxo-4,7-dihydrothieno[3,2-b]pyridine-6-carboxamide;
b) N-(4-chlorobenzyl)-2-{[[2-(2-furyl)-2-hydroxyethyl](methyl)amino]methyl}-4-methyl-7-oxo-4,7-dihydrothieno[3,2-b]pyridine-6-carboxamide;
c) N-(4-chlorobenzyl)-2-{[(2-hydroxy-2-pyrazin-2-ylethyl)(methyl)amino]methyl}-4-methyl-7-oxo-4,7-dihydrothieno[3,2-b]pyridine-6-carboxamide;
d) N-(4-chlorobenzyl)-2-{[(2-hydroxy-2-pyrimidin-2-ylethyl)(methyl)amino]methyl}-4-methyl-7-oxo-4,7-dihydrothieno[3,2-b]pyridine-6-carboxamide;
e) N-(4-chlorobenzyl)-2-{[[2-hydroxy-2-(1H-indol-3-yl)ethyl](methyl)amino]methyl}-4-methyl-7-oxo-4,7-dihydrothieno[3,2-b]pyridine-6-carboxamide; or
f) 2-{[[2-(3-aminophenyl)-2-hydroxyethyl](methyl)amino]methyl}-N-(4-chlorobenzyl)-4-methyl-7-oxo-4,7-dihydrothieno[3,2-b]pyridine-6-carboxamide;

or a pharmaceutically acceptable salt thereof.

37. A pharmaceutical composition comprising a compound of claim 1 and a pharmaceutically acceptable excipient.

38. A method of treating a herpesviral infection in a mammal, comprising: administering to an mammal in need of such treatment an effective amount of a compound of claim 1.

39. The method of claim 38 wherein the mammal is a human or animal.

40. The method of claim 38 wherein the mammal is a human.

41. The method of claim 38 wherein the mammal is an animal.

42. The method of claim 38 wherein the compound is administered in an amount of from about 0.1 to about 300 mg/kg of body weight.

43. The method of claim 38 wherein the compound is administered in an amount of from about 1 to about 30 mg/kg of body weight.

44. A method of treating atherosclerosis or restenosis comprising administering to a mammal in need thereof a compound of claim 1.

45. A method for preparing a compound of formula I:

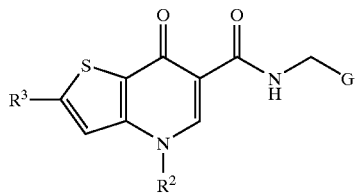

wherein G, $R^2$ and $R^3$ have the values described in claim 1, comprising: reacting a nucleophile with a compound of the formula III:

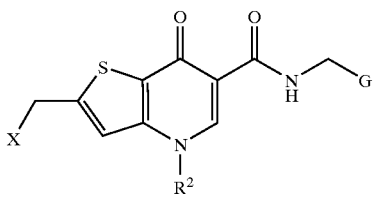

wherein X is a leaving group.

46. The method of claim 45 wherein the nucleophile is of the formula $NHR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_mR^9$, $CONR^{13}R^{13}$, $CO_2R^{13}$, $(C=O)R^9$, het, aryl, cyano, or halo substituents, and the leaving group X is halo.

47. A method for preparing a compound of formula I:

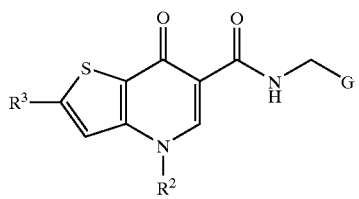

wherein G, $R^2$ and $R^3$ have the values described in claim 1 comprising: reacting a nucleophile of the formula $NH_2$—$CH_2$—G with a compound of the formula II

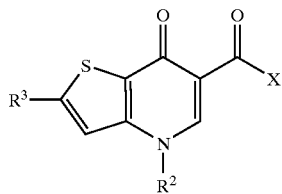

where X is a leaving group.

48. A method for preparing a compound of formula A-4:

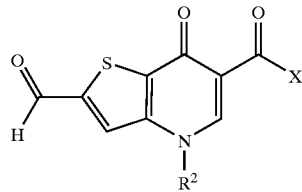

wherein $R^2$ is H, and X is a blocking group, comprising: treating a compound of formula A-3:

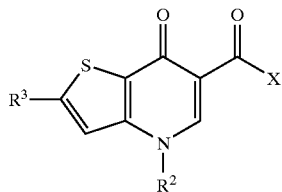

wherein $R^2$ and $R^3$ are H, with a strong aprotic base and then reacting the resulting intermediate with a formylating agent.

49. The compound (1S)-2-(methylamino)-1-pyridin-3-ylethanol; or a salt thereof.

50. A compound of formula I:

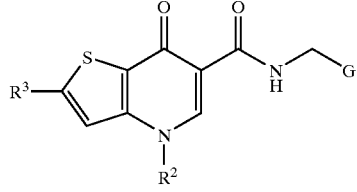

wherein:
   G is phenyl substituted with from one to five $R^1$ substituents;
   each $R^1$ is independently
      (a) Cl,
      (b) Br,
      (c) F,
      (d) cyano,
      (e) $C_{1-7}$alkyl, or
      (e) $NO_2$;
   $R^2$ is
      (a) H,
      (b) $R^5$,
      (c) $NR^7R^8$,
      (d) $SO_2R^9$, or
      (e) $OR^6$;

$R^3$ is
- (a) halo,
- (b) aryl,
- (c) $S(O)_m R^6$,
- (d) $(C=O)R^6$,
- (e) $(C=O)OH$,
- (f) $(C=O)OR^9$,
- (g) cyano,
- (h) het, wherein the het is bound via a carbon atom,
- (i) $OR^{14}$,
- (j) $NR^7 R^8$,
- (k) $SR^{14}$,
- (l) $NHSO_2 R^{12}$,
- (m) $C_{1-7}$alkyl which is optionally partially unsaturated and optionally substituted by one or more $R^{11}$ substituents, or
- (n) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^5$ is
- (a) $(CH_2 CH_2 O)_r R^{10}$,
- (b) het, wherein the het is bound via a carbon atom,
- (c) aryl,
- (d) $C_{1-7}$alkyl which is optionally partially unsaturated and optionally substituted by one or more $R^{11}$ substituents, or
- (e) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^6$ is
- (a) $C_{1-7}$alkyl optionally substituted by aryl, het, $OR^{13}$, $SR^{13}$, $NR^{13} R^{13}$, halo, or $C_{3-8}$cycloalkyl, which $C_{3-8}$cycloalkyl is optionally substituted with $OR^{13}$,
- (b) $C_{3-8}$cycloalkyl which is optionally partially unsaturated and optionally substituted by one or more halo, $OR^{13}$, $SR^{13}$, or $NR^{13} R^{13}$ substituents,
- (c) $NR^7 R^8$,
- (d) aryl, or
- (e) het, wherein the het is bound via a carbon atom;

$R^7$ and $R^8$ are independently
- a. H,
- b. aryl,
- c. $C_{1-7}$alkyl which is optionally partially unsaturated and optionally substituted by one or more $NR^{13} R^{13}$, $OR^{14}$, $SR^{14}$, $S(O)_m R^9$, $P(=O)(OR^{14})(R^{14})$, $CONR^{14} R^{14}$, $CO_2 R^{13}$, $(C=O)R^9$, het, aryl, cyano, or halo substituents,
- d. $C_{3-8}$cycloalkyl which is optionally partially unsaturated and optionally substituted by one or more halo, $OR^{13}$, $SR^{13}$, oxo, or $NR^{13} R^{13}$ substituents,
- e. $(C=O)R^9$, or
- f. $R^7$ and $R^8$ together with the nitrogen to which they are attached form a het;

$R^9$ is
- (a) aryl,
- (b) het
- (c) $C_{3-8}$cycloalkyl, or
- (d) $C_{1-7}$alkyl which is optionally partially unsaturated and optionally substituted by one or more $NR^{13} R^{13}$, $OR^{14}$, $SR^{14}$, halo, $CONR^{13} R^{13}$, $CO_2 R^{13}$, het, aryl substituents, $R^{10}$ is
- (a) H, or
- (b) $C_{1-7}$alkyl optionally substituted by OH;

$R^{11}$ is
- (a) $OR^{14}$,
- (b) $SR^{14}$,
- (c) $NR^7 R^8$,
- (d) halo,
- (e) $CONH_2$,
- (f) $CONHR^9$,
- (g) $CONR^9 R^9$,
- (h) $CO_2 H$,
- (i) $CO_2 R^9$,
- (j) het,
- (k) aryl,
- (l) cyano,
- (m) oxo,
- (p) $SO_m R^6$, or
- (q) $P(=O)(OR^{14})(R^{14})$;

$R^{12}$ is
- (a) H,
- (b) het,
- (c) aryl,
- (d) $C_{3-8}$cycloalkyl optionally substituted with $R^{11}$, or
- (e) $C_{1-7}$alkyl optionally substituted with $R^{11}$;

$R^{13}$ is
- (a) H, or
- (b) $C_{1-7}$alkyl;

$R^{14}$ is
- (a) H,
- (b) aryl,
- (c) het,
- (d) $C_{1-7}$alkyl which is optionally partially unsaturated and optionally substituted by aryl, het, $OR^{13}$, $SR^{13}$, $NR^{13} R^{13}$, halo, or $C_{3-8}$cycloalkyl which $C_{3-8}$cycloalkyl is optionally substituted by one or more $OR^{13}$, or
- (e) $C_{3-8}$cycloalkyl which is optionally partially unsaturated and optionally substituted by one or more halo, $OR^{13}$, $SR^{13}$, or $NR^{13} R^{13}$ substituents;

$R^{15}$ is
- (s) H,
- (t) halo,
- (u) $OR^{13}$,
- (v) $SR^{13}$,
- (w) $NR^{13} R^{13}$,
- (x) $O(CH_2 CH_2 O)_n R^{10}$,
- (y) phenyl,
- (z) cyano,
- (aa) nitro,
- (bb) $CONR^{13} R^{13}$,
- (cc) $CO_2 R^{13}$,
- (dd) $S(O)_m NR^{13} R^{13}$,
- (ee) $CONHR^{13}$,
- (ff) $S(O)_m R^{10}$,
- (gg) $NR^{13} COR^{13}$,
- (hh) $C_{1-7}$alkyl which is optionally partially unsaturated and optionally substituted with one or more oxo, phenyl, 4-morpholine, $OR^{13}$, $SR^{13}$, $NR^{13} R^{13}$, halo, $CO_2 R^{13}$, $CONR^{13} R^{13}$, or $C_{3-8}$cycloalkyl which $C_{3-8}$cycloalkyl is optionally substituted by one or more $OR^{13}$, or
- (ii) $C_{3-8}$cycloalkyl which is optionally partially unsaturated and optionally substituted by one or more oxo, halo, $OR^{13}$, $SR^{13}$, $C_{1-7}$alkyl, $CONH_2$ or $NR^{13} R^{13}$ substituents; or (jj) pyrimidinyl, pyridyl, pyrrolyl, pyrazinyl, pyridazinyl, imidazolyl, or pyrazolyl;

each i is independently 2, 3, or 4;

each n is independently 1, 2, 3, 4, or 5;

each m is independently 1 or 2;

wherein any aryl other than G is optionally substituted with one or more $R^{15}$ substituents; and
  wherein any het is independently a 4–16 member saturated or unsaturated monocyclic, bicyclic, or tricyclic ring system having 1, 2, 3, or 4 heteroatoms selected from oxygen, sulfur, sulfinyl, sulfonyl, nitrogen, and an N-oxide and is optionally substituted with one or more =O, =N—$OR^{13}$, or $R^{15}$ substituents; or a pharmaceutically acceptable salt thereof.

* * * * *